(12) United States Patent
Meek et al.

(10) Patent No.: US 11,832,856 B2
(45) Date of Patent: Dec. 5, 2023

(54) BONE-FIXATION DEVICE AND SYSTEM

(71) Applicant: The University of British Columbia, Vancouver (CA)

(72) Inventors: Robert N. Meek, Vancouver (CA); Carly Anderson Thaler, Seattle, WA (US); Steven Charles Dimmer, Bellevue, WA (US)

(73) Assignee: The University of British Columbia, Vancouver (CA)

( * ) Notice: Subject to any disclaimer, the term of this patent is extended or adjusted under 35 U.S.C. 154(b) by 0 days.

(21) Appl. No.: 17/286,388

(22) PCT Filed: Oct. 17, 2019

(86) PCT No.: PCT/CA2019/051471
§ 371 (c)(1),
(2) Date: Apr. 16, 2021

(87) PCT Pub. No.: WO2020/077457
PCT Pub. Date: Apr. 23, 2020

(65) Prior Publication Data
US 2021/0353338 A1 Nov. 18, 2021

Related U.S. Application Data

(60) Provisional application No. 62/905,925, filed on Sep. 25, 2019, provisional application No. 62/747,039, filed on Oct. 17, 2018.

(51) Int. Cl.
*A61B 17/74* (2006.01)
*A61B 17/72* (2006.01)
(Continued)

(52) U.S. Cl.
CPC ............ *A61B 17/742* (2013.01); *A61B 17/70* (2013.01); *A61B 17/72* (2013.01);
(Continued)

(58) Field of Classification Search
None
See application file for complete search history.

(56) References Cited

U.S. PATENT DOCUMENTS

| 2,328,270 A | 8/1943 | Daniel |
| 2,724,573 A | 11/1955 | Lundquist |

(Continued)

FOREIGN PATENT DOCUMENTS

| AT | 509852 | 12/2011 |
| AT | 509852 A4 | 12/2011 |

(Continued)

OTHER PUBLICATIONS

International Bureau, "International Preliminary Report on Patentability from PCT Application No. PCT/CA2019/051471", from Foreign Counterpart to U.S. Appl. No. 17/286,388, filed Apr. 29, 2021, pp. 1 through 9, Published: WO.

(Continued)

*Primary Examiner* — Tessa M Matthews
(74) *Attorney, Agent, or Firm* — FORTEM IP, LLP; Suzannah Beeman; Mary Fox

(57) ABSTRACT

The current invention features a rod screw for medical application that can be configured and used to fixate fracture of bones varying in shape and dimension, and treating maladies such as scoliosis, and securing an implanted device, to tissue such as bone. This is achieved by designing a flexible rod screw with a mechanism to lock the configuration in a rigid state. In an embodiment, a bone-fracture fixation device, such as a rod screw, includes a flexible body, a plurality of flexible members, and first and second interfaces. The flexible members are disposed longitudinally within the flexible body, such that the flexible body is rigid when the flexible members are fixed into position. And the first and second interfaces are respectively coupled to the flexible body, each of at least one of the first and second (Continued)

interfaces including a respective at least one hole each configured to receive a respective attachment member configured to engage a bone.

21 Claims, 28 Drawing Sheets

(51) Int. Cl.
 *A61B 17/88* (2006.01)
 *A61B 17/70* (2006.01)
(52) U.S. Cl.
 CPC ...... *A61B 17/7208* (2013.01); *A61B 17/7233* (2013.01); *A61B 17/8897* (2013.01)

(56) References Cited

U.S. PATENT DOCUMENTS

| | | | |
|---|---|---|---|
| 3,371,725 A | 3/1968 | Wilhelm et al. | |
| 4,098,351 A | 7/1978 | Alessio | |
| 4,489,792 A | 12/1984 | Fahim et al. | |
| 4,491,443 A | 1/1985 | Decaro | |
| 4,605,348 A | 8/1986 | Decaro | |
| 4,706,659 A | 11/1987 | Matthews et al. | |
| 5,108,397 A | 4/1992 | White | |
| 5,167,665 A | 12/1992 | Mckinney | |
| 5,234,435 A | 8/1993 | Seagrave, Jr. | |
| D346,218 S | 4/1994 | White | |
| 5,300,071 A | 4/1994 | Browner et al. | |
| 5,336,224 A | 8/1994 | Selman | |
| 5,527,309 A | 6/1996 | Shelton | |
| 5,527,310 A | 6/1996 | Cole et al. | |
| 5,593,407 A | 1/1997 | Reis | |
| 5,601,550 A | 2/1997 | Esser | |
| 5,649,925 A | 7/1997 | Barbera Alacreu | |
| 5,879,352 A | 3/1999 | Filoso et al. | |
| 5,944,719 A | 8/1999 | Leban | |
| 5,993,454 A | 11/1999 | Longo | |
| 6,209,886 B1 | 4/2001 | Estes et al. | |
| 6,340,362 B1 | 1/2002 | Pierer et al. | |
| 6,368,326 B1 | 4/2002 | Dakin et al. | |
| 7,258,692 B2 | 8/2007 | Thelen et al. | |
| 7,410,483 B2 | 8/2008 | Danitz et al. | |
| 7,625,395 B2 | 12/2009 | Muckter et al. | |
| 7,632,277 B2 | 12/2009 | Woll et al. | |
| 7,785,325 B1 | 8/2010 | Milbank | |
| 7,846,162 B2 | 12/2010 | Nelson et al. | |
| 8,043,347 B2 | 10/2011 | Jiang et al. | |
| 8,128,626 B2 | 3/2012 | Justin | |
| 8,128,627 B2 | 3/2012 | Justin et al. | |
| 8,206,389 B2 | 6/2012 | Huebner et al. | |
| 8,372,074 B2 | 2/2013 | Milbank | |
| 8,409,257 B2 | 4/2013 | Edidin et al. | |
| 8,439,916 B2 | 5/2013 | Coati et al. | |
| 8,632,543 B2 | 1/2014 | Metzinger et al. | |
| 8,961,516 B2 | 2/2015 | Nelson et al. | |
| 9,060,809 B2 | 6/2015 | Tipirneni et al. | |
| 9,144,506 B2 | 9/2015 | Phelps | |
| 9,155,574 B2 | 10/2015 | Saravia et al. | |
| 9,482,260 B1 | 11/2016 | Krause | |
| 9,498,264 B2 | 11/2016 | Harshman et al. | |
| 9,532,789 B2 | 1/2017 | Coope | |
| 9,615,835 B2 | 4/2017 | Lam et al. | |
| 9,839,435 B2 | 12/2017 | Meek et al. | |
| 10,258,394 B2 | 4/2019 | Harshman et al. | |
| 10,307,188 B2 | 6/2019 | Harshman et al. | |
| 10,973,559 B2 | 4/2021 | Harshman et al. | |
| 11,369,421 B2 | 6/2022 | Harshman et al. | |
| 11,419,645 B2 | 8/2022 | Stinson et al. | |
| 11,529,148 B2 | 12/2022 | Meek et al. | |
| 2002/0032444 A1 | 3/2002 | Mische | |
| 2002/0077631 A1 | 6/2002 | Lubbers et al. | |
| 2002/0087161 A1 | 7/2002 | Randall et al. | |
| 2002/0198527 A1 | 12/2002 | Muckter | |
| 2003/0078582 A1 | 4/2003 | Heggeness | |
| 2003/0181982 A1 | 9/2003 | Kuslich | |
| 2003/0187449 A1 | 10/2003 | McCleary et al. | |
| 2003/0229351 A1 | 12/2003 | Tidwell et al. | |
| 2004/0011565 A1 | 1/2004 | Lyon et al. | |
| 2004/0024409 A1 | 2/2004 | Sand et al. | |
| 2004/0050568 A1 | 3/2004 | Orozco | |
| 2004/0102778 A1 | 5/2004 | Huebner et al. | |
| 2004/0215191 A1 | 10/2004 | Kitchen | |
| 2005/0055023 A1 | 3/2005 | Sohngen et al. | |
| 2005/0085819 A1 | 4/2005 | Ellis et al. | |
| 2005/0154390 A1 | 7/2005 | Biedermann et al. | |
| 2005/0165401 A1 | 7/2005 | Pack | |
| 2006/0074421 A1 | 4/2006 | Bickley et al. | |
| 2006/0264950 A1 | 11/2006 | Nelson et al. | |
| 2007/0083204 A1 | 4/2007 | Sidebotham | |
| 2007/0162132 A1 | 7/2007 | Messerli | |
| 2007/0208364 A1 | 9/2007 | Smith et al. | |
| 2007/0233111 A1 | 10/2007 | Orbay et al. | |
| 2008/0051786 A1 | 2/2008 | Jensen | |
| 2008/0058722 A1 | 3/2008 | Von Oepen et al. | |
| 2008/0077133 A1 | 3/2008 | Schulze | |
| 2008/0077154 A1 | 3/2008 | Edwards et al. | |
| 2008/0108989 A1 | 5/2008 | Parsell et al. | |
| 2008/0161805 A1 | 7/2008 | Saravia et al. | |
| 2008/0181740 A1 | 7/2008 | Waitszies | |
| 2008/0195145 A1 | 8/2008 | Bonutti et al. | |
| 2008/0234676 A1 | 9/2008 | Schulze et al. | |
| 2008/0249628 A1 | 10/2008 | Altarac et al. | |
| 2008/0269745 A1 | 10/2008 | Justin | |
| 2008/0287951 A1 | 11/2008 | Stoneburner et al. | |
| 2008/0294163 A1 | 11/2008 | Chou et al. | |
| 2008/0294164 A1* | 11/2008 | Frank | A61B 17/744 606/301 |
| 2008/0319455 A1 | 12/2008 | Harris et al. | |
| 2009/0024174 A1 | 1/2009 | Stark | |
| 2009/0048672 A1 | 2/2009 | Essenmacher | |
| 2009/0062797 A1 | 3/2009 | Huebner et al. | |
| 2009/0149710 A1 | 6/2009 | Stefanchik et al. | |
| 2009/0192512 A1 | 7/2009 | Sommers | |
| 2009/0216232 A1 | 8/2009 | Buford, III et al. | |
| 2009/0228008 A1 | 9/2009 | Justin et al. | |
| 2009/0299343 A1 | 12/2009 | Rogers | |
| 2010/0023010 A1 | 1/2010 | Nelson et al. | |
| 2010/0076503 A1 | 3/2010 | Beyar et al. | |
| 2010/0185290 A1 | 7/2010 | Compton et al. | |
| 2010/0217333 A1 | 8/2010 | McShane et al. | |
| 2010/0249832 A1 | 9/2010 | Stopek et al. | |
| 2010/0249838 A1 | 9/2010 | Stopek et al. | |
| 2010/0249854 A1 | 9/2010 | Thomas et al. | |
| 2010/0249944 A1 | 9/2010 | Thomas et al. | |
| 2010/0262239 A1 | 10/2010 | Boyden et al. | |
| 2010/0286692 A1 | 11/2010 | Greenhalgh et al. | |
| 2010/0298893 A1 | 11/2010 | Stucki | |
| 2010/0318137 A1 | 12/2010 | Stucki et al. | |
| 2010/0331842 A1 | 12/2010 | Milbank | |
| 2011/0015684 A1 | 1/2011 | Belcheva et al. | |
| 2011/0028974 A1 | 2/2011 | Chemello | |
| 2011/0040282 A1 | 2/2011 | Uihlein | |
| 2011/0046746 A1 | 2/2011 | Rabiner et al. | |
| 2011/0087227 A1 | 4/2011 | Mazur et al. | |
| 2011/0098757 A1 | 4/2011 | Schelling | |
| 2011/0098816 A1 | 4/2011 | Jacob et al. | |
| 2011/0098817 A1 | 4/2011 | Eckhardt et al. | |
| 2011/0119815 A1 | 5/2011 | Paulson et al. | |
| 2011/0144643 A1 | 6/2011 | Lorenz et al. | |
| 2011/0144645 A1 | 6/2011 | Saravia et al. | |
| 2011/0144703 A1 | 6/2011 | Krause et al. | |
| 2011/0153454 A1 | 6/2011 | Dunn et al. | |
| 2011/0184518 A1 | 7/2011 | Trieu | |
| 2011/0184519 A1 | 7/2011 | Trieu | |
| 2011/0184520 A1 | 7/2011 | Trieu | |
| 2011/0196435 A1 | 8/2011 | Forsell | |
| 2011/0230966 A1 | 9/2011 | Trieu | |
| 2011/0238181 A1 | 9/2011 | Trieu | |
| 2011/0264229 A1 | 10/2011 | Donner | |
| 2011/0288598 A1 | 11/2011 | Moed et al. | |
| 2011/0306975 A1 | 12/2011 | Kaikkonen et al. | |
| 2011/0319944 A1 | 12/2011 | Borodic | |
| 2012/0010617 A1 | 1/2012 | Maza | |

(56) References Cited

U.S. PATENT DOCUMENTS

| | | | |
|---|---|---|---|
| 2012/0065638 A1 | 3/2012 | Moore | |
| 2012/0078252 A1 | 3/2012 | Huebner et al. | |
| 2012/0078311 A1 | 3/2012 | Huebner et al. | |
| 2012/0083847 A1 | 4/2012 | Huebner et al. | |
| 2012/0083895 A1 | 4/2012 | Conway et al. | |
| 2012/0101533 A1 | 4/2012 | Purcell et al. | |
| 2012/0101576 A1 | 4/2012 | Dewey et al. | |
| 2013/0006145 A1 | 1/2013 | Toomey et al. | |
| 2013/0006245 A1 | 1/2013 | Stoneburner et al. | |
| 2013/0012942 A1 | 1/2013 | Nelson et al. | |
| 2013/0131678 A1 | 5/2013 | Dahners | |
| 2013/0144348 A1 | 6/2013 | Schwappach | |
| 2013/0325007 A1 | 12/2013 | Beyar et al. | |
| 2014/0114312 A1 | 4/2014 | Krause | |
| 2014/0296853 A1* | 10/2014 | Wolter | A61B 17/725 606/64 |
| 2014/0309636 A1 | 10/2014 | Meek et al. | |
| 2014/0358146 A1 | 12/2014 | Meek et al. | |
| 2015/0038970 A1 | 2/2015 | Coope | |
| 2015/0157370 A1 | 6/2015 | Gross | |
| 2015/0257800 A1* | 9/2015 | Harshman | A61B 17/1717 606/62 |
| 2015/0297245 A1 | 10/2015 | Lam et al. | |
| 2017/0014170 A1 | 1/2017 | Fallin et al. | |
| 2017/0020585 A1 | 1/2017 | Harshman et al. | |
| 2017/0049460 A1 | 2/2017 | Coope | |
| 2017/0164953 A1 | 6/2017 | Lam et al. | |
| 2017/0238977 A1* | 8/2017 | Harshman | A61B 17/7208 |
| 2018/0092681 A1 | 4/2018 | Lutz | |
| 2018/0296227 A1 | 10/2018 | Meek et al. | |
| 2019/0231401 A1 | 8/2019 | Harshman et al. | |
| 2019/0282280 A1 | 9/2019 | Harshman et al. | |
| 2020/0054372 A1 | 2/2020 | Stinson et al. | |
| 2020/0138492 A1* | 5/2020 | Kavanagh | A61B 17/8052 |
| 2021/0220027 A1 | 7/2021 | Harshman et al. | |
| 2021/0322070 A1* | 10/2021 | Koch | A61B 17/7283 |
| 2021/0386465 A1 | 12/2021 | Thaler et al. | |
| 2022/0287744 A1 | 9/2022 | Harshman et al. | |
| 2022/0354549 A1 | 11/2022 | Stinson et al. | |

FOREIGN PATENT DOCUMENTS

| | | |
|---|---|---|
| CN | 2662839 Y | 12/2004 |
| CN | 2699846 | 5/2005 |
| CN | 2699846 Y | 5/2005 |
| CN | 101208053 A | 6/2008 |
| CN | 101633119 A | 1/2010 |
| CN | 101636119 A | 1/2010 |
| CN | 102793579 A | 11/2012 |
| CN | 103200887 A | 7/2013 |
| CN | 103813764 A | 5/2014 |
| CN | 104203132 A | 12/2014 |
| CN | 104203132 B | 8/2017 |
| CN | 107106217 A | 8/2017 |
| CN | 112955087 A | 6/2021 |
| EP | 0078619 A2 | 5/1983 |
| EP | 1941838 A1 | 7/2008 |
| EP | 2779928 A1 | 9/2014 |
| EP | 3326558 A1 | 5/2018 |
| EP | 3206608 | 7/2018 |
| EP | 3206608 A4 | 7/2018 |
| EP | 3522803 A1 | 8/2019 |
| EP | 3866712 A1 | 8/2021 |
| GB | 1494553 A | 12/1977 |
| WO | 2007009123 A2 | 1/2007 |
| WO | 2008116175 A2 | 9/2008 |
| WO | 2008120877 A1 | 10/2008 |
| WO | 2009143374 A2 | 11/2009 |
| WO | 2010124230 A1 | 10/2010 |
| WO | 2011067668 A1 | 6/2011 |
| WO | 2011119815 A2 | 9/2011 |
| WO | 2011153454 A2 | 12/2011 |
| WO | 2012107913 A2 | 8/2012 |
| WO | 2013063145 A1 | 5/2013 |
| WO | 2013071432 A1 | 5/2013 |
| WO | 2014075165 A1 | 5/2014 |
| WO | 2014075184 A1 | 5/2014 |
| WO | 2015134750 A1 | 9/2015 |
| WO | 2016061173 A1 | 4/2016 |
| WO | 2018067888 A1 | 4/2018 |
| WO | 2020077457 A1 | 4/2020 |
| WO | 2020081855 A1 | 4/2020 |

OTHER PUBLICATIONS

U.S. Patent and Trademark Office, "Office Action", U.S. Appl. No. 15/952,093, dated May 13, 2021, pp. 1 through 25, Published: US.

U.S. Patent and Trademark Office, "Advisory Action", U.S. Appl. No. 16/414,435, dated Apr. 24, 2021, pp. 1 Through 4, Published: US.

European Patent Office, "Communication pursuant to Article 94(3) EPC from EP Application No. 15850096.7", from Foreign Counterpart to U.S. Appl. No. 15/519,148, dated Oct. 5, 2021, pp. 1 through 5, Published: EP.

State Intellectual Property Office, P.R. China, "Third Office Action from CN Application No. 201280066180.2 dated Jan. 5, 2017", from Foreign Counterpart to U.S. Appl. No. 14/357,917, filed Jan. 5, 2017, pp. 1-4, Published: CN.

U.S. Patent and Trademark Office, "Advisory Action", U.S. Appl. No. 14/300,752, dated Feb. 16, 2017, pp. 1-3, Published: US.

U.S. Patent and Trademark Office, "Advisory Action", U.S. Appl. No. 14/300,752, dated Oct. 7, 2015, pp. 1-3, Published: US.

U.S. Patent and Trademark Office, "Advisory Action", U.S. Appl. No. 15/952,093, dated Jan. 13, 2021, pp. 1 through 6, Published: US.

Vaidya, R., et al., "Complications of Anterior Subcutaneous Internal Fixation for Unstable Pelvis Fractures: A Multicenter Study," Clinical Orthopaedicsand Related Research, Aug. 2012, pp. 1-8 vol. 470, No. 8, Springer.

U.S. Patent and Trademark Office, "Final Office Action", U.S. Appl. No. 14/300,752, dated Jan. 12, 2018, pp. 1-37, Published: US.

U.S. Patent and Trademark Office, "Final Office Action", U.S. Appl. No. 14/300,752, dated May 28, 2015, pp. 1-14, Published: US.

U.S. Patent and Trademark Office, "Final Office Action", U.S. Appl. No. 14/300,752, dated Nov. 3, 2016, pp. 1-15, Published: US.

U.S. Patent and Trademark Office, "Final Office Action", U.S. Appl. No. 14/357,917, dated Sep. 6, 2016, pp. 1-11, Published: US.

U.S. Patent and Trademark Office, "Final Office Action", U.S. Appl. No. 15/952,093, dated Sep. 25, 2020, pp. 1 through 19, Published: US.

U.S. Patent and Trademark Office, "Interview Summary" U.S. Appl. No. 14/727,576, dated Feb. 17, 2016, pp. 1-4, Published: US.

U.S. Patent and Trademark Office, "Interview Summary", U.S. Appl. No. 14/727,576, dated Jun. 14, 2016, pp. 1-3, Published: US.

U.S. Patent and Trademark Office, "Notice of Allowance" U.S. Appl. No. 14/727,576, dated Jul. 19, 2016, pp. 1-8, Published: US.

U.S. Patent and Trademark Office, "Notice of Allowance", U.S. Appl. No. 14/357,917, dated Jul. 26, 2017, pp. 1-5, Published: US.

U.S. Patent and Trademark Office, "Notice of Allowance", U.S. Appl. No. 15/285,811, dated Mar. 25, 2019, pp. 1-11, Published: US.

U.S. Patent and Trademark Office, "Notice of Allowance", U.S. Appl. No. 15/519,148, dated Feb. 13, 2019, pp. 1-42, Published: US.

U.S. Patent and Trademark Office, "Notice of Allowance", U.S. Appl. No. 16/384,758, dated Dec. 2, 2020, pp. 1 through 21, Published: US.

U.S. Patent and Trademark Office, "Office Action for U.S. Appl. No. 15/285,811 dated Oct. 18, 2018", pp. 1-39, Published in: US.

U.S. Patent and Trademark Office, "Office Action", U.S. Appl. No. 14/300,752, dated Apr. 5, 2016, pp. 1-16, Published: US.

U.S. Patent and Trademark Office, "Office Action", U.S. Appl. No. 14/300,752, dated Aug. 8, 2017, pp. 1-16, Published: US.

U.S. Patent and Trademark Office, "Office Action", U.S. Appl. No. 14/300,752, dated Oct. 20, 2014, pp. 1-14, Published: US.

U.S. Patent and Trademark Office, "Office Action", U.S. Appl. No. 14/357,917, dated Apr. 18, 2016, pp. 1-10, Published: US.

(56) References Cited

OTHER PUBLICATIONS

U.S. Patent and Trademark Office, "Office Action", U.S. Appl. No. 14/727,576, dated Oct. 16, 2015, pp. 1-14, Published: US.
U.S. Patent and Trademark Office, "Office Action", U.S. Appl. No. 14/727,576, dated Apr. 28, 2016, pp. 1-15, Published: US.
U.S. Patent and Trademark Office, "Office Action", U.S. Appl. No. 15/519,148, dated Jul. 26, 2018, pp. 1-38, Published: US.
U.S. Patent and Trademark Office, "Office Action", U.S. Appl. No. 15/952,093, dated Mar. 6, 2020, pp. 1-71, Published: US.
U.S. Patent and Trademark Office, "Office Action", U.S. Appl. No. 16/384,758, dated Jul. 24, 2020, pp. 1 through 69, Published: US.
U.S. Patent and Trademark Office, "Office Action", U.S. Appl. No. 16/414,435, dated Jul. 14, 2020, pp. 1 through 62, Published: US.
U.S. Patent and Trademark Office, "Restriction Requirement", U.S. Appl. No. 14/357,917, dated Jan. 21, 2016, pp. 1-6, Published: US.
U.S. Patent and Trademark Office, "Restriction Requirement", U.S. Appl. No. 14/727,576, dated Jul. 23, 2015. pp. 1-10, Published: US.
U.S. Patent and Trademark Office, "Restriction Requirement", U.S. Appl. No. 15/285,811, dated Mar. 30, 2018, pp. 1-7, Published: US.
U.S. Patent and Trademark Office, "Restriction Requirement", U.S. Appl. No. 15/952,093, dated Nov. 29, 2019, pp. 1 through 8, Published: US.
U.S. Patent and Trademark Office, "Restriction Requirement", U.S. Appl. No. 16/340,067, dated Dec. 16, 2020, pp. 1 through 7, Published: US.
U.S. Pat. No. 7,273,482, (withdrawn).
U.S. Patent and Trademark Office, "Final Office Action", U.S. Appl. No. 16/414,435, dated Mar. 22, 2021, pp. 1 through 26, Published: US.
Novick, "Pelvic Fractures/Acetabular Fractures", Hospital for Special Surgery, Mar. 30, 2006, pp. 1-9, HSS.edu.
"UT Southwest Medical Surgeons Market Pelvic Fracture Device," accessed at http://www.texasbusiness.com/ut-southwest-medical-surgeons-market-pelvic-fracture-device-cms-4418, Apr. 22, 2011, pp. 1-5, Texas Business.com.
Australian Government IP Australia, "Examination report No. 1 for standard patent application from AU Application No. 2015333623 dated Sep. 26, 2017", from Foreign Counterpart to U.S. Appl. No. 15/519,148, filed Sep. 26, 2017, pp. 1-4, Published: AU.
Australian Government IP Australia, "Notice of acceptance for patent application from AU Application No. 2015333623 dated Jul. 20, 2018", from Foreign Counterpart to PCT Application No. PCT/US2015/055441, Jul. 20, 2018, pp. 1-3, Published: AU.
Australian Government IP Australia, "Notice of Acceptance from AU Application No. 2012339536 dated Jan. 28, 2016", from Foreign Counterpart to PCT Application No. PCT/CA2012/050808, Jan. 28, 2016, pp. 1-3, Published: AU.
Australian Government IP Australia, "Patent Examination Report No. 1 from AU Application No. 2012339536 dated Jan. 23, 2015", from Foreign Counterpart to U.S. Appl. No. 14/357,917, filed Jan. 23, 2015, pp. 1-5, Published: AU.
Australian Government IP Australia, "Patent Examination Report No. 2 from AU Application No. 2012339536 dated Oct. 16, 2015", from Foreign Counterpart to U.S. Appl. No. 14/357,917, filed Oct. 16, 2015, pp. 1-6, Published: AU.
Barry et al., "Flexible intramedullary nails for fractures in children", Aspects of Current Management, Sep. 2004, pp. 1-7, vol. 86-B, No. 7, British Editorial Society of Bone and Joint Surgery.
Canadian Intellectual Property Office, "Notice of Allowance from CA Application No. 2964370", from Foreign Counterpart to U.S. Appl. No. 15/519,148, dated Dec. 13, 2019, p. 1, Published: CA.
Canadian Intellectual Property Office, "Office Action from CA Application No. 2,855,752 dated Feb. 3, 2017", from Foreign Counterpart to U.S. Appl. No. 14/357,917, filed Feb. 3, 2017, pp. 1-4, Published: CA.
Canadian Intellectual Property Office, "Office Action from CA Application No. 2,855,752 dated Mar. 9, 2018", from Foreign Counterpart to U.S. Appl. No. 14/357,917, filed Mar. 9, 2018, pp. 1-5, Published: CA.

Canadian Intellectual Property Office, "Office Action from CA Application No. 2,855,752 dated Oct. 28, 2015", from Foreign Counterpart to U.S. Appl. No. 14/357,917, filed Oct. 28, 2015, pp. 1-4, Published: CA.
Canadian Intellectual Property Office, "Office Action from CA Application No. 2,964,370 dated Jan. 24, 2019", from Foreign Counterpart to U.S. Appl. No. 15/519,148, filed Jan. 24, 2019, pp. 1-6, Published: CA.
Canadian Intellectual Property Office, "Office Action from CA Application No. 2,964,370 dated May 4, 2018", from Foreign Counterpart to PCT Application No. PCT/US2015/055441, May 4, 2018, pp. 1-7, Published: CA.
Canadian Intellectual Property Office, "Office Action from CA Application No. 2855752 dated Jun. 17, 2019", from Foreign Counterpart to U.S. Appl. No. 14/357,917, pp. 1-3, Published: CA.
Canadian Intellectual Property Office, "Office Action from CA Application No. 2978697 dated Oct. 19, 2018", from Foreign Counterpart to PCT Application No. PCT/US2015/018969, Oct. 19, 2018, pp. 1-4, Published: CA.
Cheung, et al., "A new halo-pelvic apparatus", Spine, (2003), vol. 28, No. 3, pp. 1-8.
China National Intellectual Property Administration, "First Office Action from CN Application No. 201580061380.2", from Foreign Counterpart to U.S. Appl. No. 16/384,758, filed Dec. 21, 2018, pp. 1 through 18, Published: CN.
State Intellectual Property Office, P.R. China, "Search Report from CN Application No. 201280066180.2 dated Aug. 10, 2016", from Foreign Counterpart to U.S. Appl. No. 14/357,917, filed Aug. 10, 2016, pp. 1-3, Published: CN.
China National Intellectual Property Administration, "Notice of Decision of Granting Patent Right for Invention from CN Application No. 201580061380.2 dated Sep. 10, 2019", from Foreign Counterpart to U.S. Appl. No. 15/519,148, pp. 1-5, Published: CN.
China National Intellectual Property Office, "Office Action from CN Application No. 201580061380.2 dated Dec. 21, 2018", from Foreign Counterpart to U.S. Appl. No. 15/519,148, filed Dec. 21, 2018, pp. 1-18, Published: CN.
European Patent Office, "Communication pursuant to Article 94(3) EPC from EP Application No. 15850096.7", from Foreign Counterpart to U.S. Appl. No. 15/519,148, filed Sep. 21, 2020, pp. 1 through 4, Published: EP.
European Patent Office, "Communication pursuant to Article 94(3) EPC from EP Application No. 17207050.0", from Foreign Counterpart to U.S. Appl. No. 14/357,917, filed Aug. 26, 2020, pp. 1 through 3, Published: EP.
European Patent Office, "Communication pursuant to Article 94(3) from EP Application No. 12849005.9 dated Jun. 2, 2016", from Foreign Counterpart to U.S. Appl. No. 14/357,917, filed Jun. 2, 2016, pp. 1-4, Published: EP.
European Patent Office, "Communication pursuant to Article 94(3) from EP Application No. 12849005.9 dated Nov. 25, 2016", from Foreign Counterpart to PCT Application No. PCT/CA2012/050808, Nov. 25, 2016, pp. 1-4, Published: EP.
European Patent Office, "Communication pursuant to Article 94(3) from EP Application No. 15850096.7", from Foreign Counterpart to U.S. Appl. No. 15/519,148, filed Oct. 15, 2019, pp. 1-5, Published: EP.
European Patent Office, "Communication pursuant to Article 94(3) from U.S. Appl. No. 14/357,917 dated Jul. 22, 2019", from Foreign Counterpart to U.S. Appl. No. 14/357,917, pp. 1-5, Published: EP.
European Patent Office, "Communication under Rule 71(3) from EP Application No. 12849005.9 dated Jul. 25, 2017", from Foreign Counterpart to U.S. Appl. No. 14/357,917, filed Jul. 25, 2017, pp. 1-6, Published: EP.
European Patent Office, "Extended European Search Report from EP Application No. 12849005.9 dated Jun. 15, 2015", from Foreign Counterpart to PCT Application No. PCT/CA2012/050808, Jun. 15, 2015, pp. 1-6, Published: EP.
European Patent Office, "Extended European Search Report from EP Application No. 15850096.7 dated Jun. 8, 2018", from Foreign Counterpart to U.S. Appl. No. 15/519,148, dated Jun. 8, 2018, pp. 1-12, Published: EP.

(56) References Cited

OTHER PUBLICATIONS

European Patent Office, "Extended European Search Report from EP Application No. 17207050.0 dated Apr. 20, 2018", from Foreign Counterpart to U.S. Appl. No. 14/357,917, filed Apr. 20, 2018, pp. 1-6, Published: EP.
European Patent Office, "Extended European Search Report from EP Application No. 17859233.3", from Foreign Counterpart to U.S. Appl. No. 16/340,067, dated Apr. 23, 2020, pp. 1 through 8, Published: EP.
Ganz, et al., "Surgical dislocation of the adult hip", The Journal of Bone and Joint Surgery (Br), Nov. 2004, pp. 1119-1124, vol. 83-B, No. 8, British Editorial Society of Bone and Joint Surgery.
Griffin et al., "Vertically Unstable Pelvic Fractures Fixed with Percutaneous Iliosacral Screws: Does Posterior Injury Pattern Prediction Fixation Failure?", Journal of Orthopedic Trauma, Jan. 2006, pp. 399-405, vol. 17, No. 6, Lippincott Williams, and Wilkins, Inc.
International Bureau, "International Preliminary Report on Patentability from PCT Application No. PCT/CA2012/050808 dated May 20, 2014", from Foreign Counterpart to U.S. Appl. No. 14/357,917, filed May 20, 2014, pp. 1-6, Published: Switzerland.
International Bureau, "International Preliminary Report on Patentability from PCT Application No. PCT/US2017/055442 dated Apr. 18, 2019", from Foreign Counterpart to U.S. Appl. No. 16/340,067, pp. 1-8, Published: WO.
International Searching Authority, "International Search Report and Written Opinion from PCT Application No. PCT/CA2012/050808 dated Feb. 26, 2013", from Foreign Counterpart to U.S. Appl. No. 14/357,917, filed Feb. 26, 2013, pp. 1-9, Published: CA.
International Searching Authority, "International Search Report and Written Opinion from PCT Application No. PCT/CA2019/051471", dated Feb. 5, 2020, pp. 1-14, Published: WO.
International Searching Authority, "International Search Report and Written Opinion from PCT Application No. PCT/US2015/055441 dated Feb. 9, 2016", from Foreign Counterpart to U.S. Appl. No. 15/519,148, filed Feb. 9, 2016, pp. 1-15, Published: US.
International Searching Authority, "International Search Report and Written Opinion from PCT Application No. PCT/US2017/055442 dated Dec. 11, 2017", Dec. 11, 2017, pp. 1-14, Published: US.
International Searching Authority, "International Search Report and Written Opinion of the International Searching Authority from PCT Application No. PCT/US15/18969 dated May 27, 2015", from Foreign Counterpart to U.S. Appl. No. 14/727,576, filed May 27, 2015, pp. 1-6, Published: US.
Japanese Patent Office, "Decision to Grant from JP Application No. 2017519539 dated Jul. 31, 2018", from Foreign Counterpart to PCT Application No. PCT/US2015/055441, Jul. 31, 2018, pp. 1-3, Published: JP.
Japanese Patent Office, "Office Action from JP Application No. 2017519539 dated Jan. 10, 2018", from Foreign Counterpart to PCT Application No. PCT/US2015/055441, Jan. 10, 2018, pp. 1-6, Published: JP.
Miller et al., "Variations in Sacral Morphology and Implications for Iliosacral Screw Fixation", Journal of the American Academy of Orthopaedic Surgeons, Jan. 2012, pp. 8-16, vol. 20, No. 1, American Academy of Orthopaedic Surgeons.
Novick, "Pelvic Fractures/Fractures of the Acetabulum", Hospital for Special Surgery, Mar. 30, 2006, pp. 1-10.
Starr et al., "Superior Pubic Ramus Fractures Fixed With Percutaneous Screws: What Predicts Fixation Failure?", Journal of Orthopaedic Trauma, Feb. 2008, pp. 81-87, vol. 22, No. 2, Lippincott Williams and Wilkins.
Starr, "Fractures of the Pelvic Ring," in Rockwood & Green's Fractures in Adults 6th Edition, Chapter-41, accessed on Feb. 4, 2014, pp. 1-40, Lippincott Williams & Wilkins.
State Intellectual Property Office Of P.R. China, "Notification on Grant of the Patent Right for Invention from CN Application No. 2012800661802 dated Apr. 28, 2017", from Foreign Counterpart to PCT Application No. PCT/CA2012/050808, Apr. 28, 2017, pp. 1-3, Published: CN.
State Intellectual Property Office, P.R. China, "Office Action from CN Application No. 201280066180.2 dated Aug. 3, 2016", from Foreign Counterpart to U.S. Appl. No. 14/357,917, filed Aug. 3, 2016, pp. 1-6, Published: CN.
State Intellectual Property Office, P.R. China, "Office Action from CN Application No. 201280066180.2 dated Dec. 28, 2015", from Foreign Counterpart to U.S. Appl. No. 14/357,917, filed Dec. 28, 2015, pp. 1-7, Published: CN.
"UT Southwest Medical Surgeons Market Pelvic Fracture Device", Accessed at http://www.texasbusiness.com/ut-southwest-medical-surgeons-market-pelvic-fracture-device-cms-4418, Texas Business. com, Apr. 22, 2011, pp. 1-5.
Barry et al., "Flexible intramedullary nails for fractures in children", Aspects of Current Management, vol. 86-B, No. 7, British Editorial Society of Bone and Joint Surgery, Sep. 2004, pp. 1-7.
Cheung et al., "A New Halo-Pelvic Apparatus", Spine, vol. 28, No. 3, pp. 305-308.
Ganz et al., "Surgical dislocation of the adult hip", The Journal of Bone and Joint Surgery (Br), vol. 83-B, No. 8, British Editorial Society of Bone and Joint Surgery, Nov. 2004, pp. 1119-1124.
Griffin et al., "Vertically Unstable Pelvic Fractures Fixed with Percutaneous Iliosacral Screws: Does Posterior Injury Jattem Prediction Fixation Failure?", Journal of Orthopedic Trauma, vol. 17, No. 6, Lippincott Williams and Wilkins, Inc., Jan. 2006, pp. 399-405.
Miller et al., "Variations in Sacral Morphology and Implications for Iliosacral Screw Fixation", Journal of the American Academy of Orthopaedic Surgeons, vol. 20, No. 1, American Academy of Orthopaedic Surgeons, Jan. 2012, pp. 8-16.
Novick, "Pelvic Fractures/Acetabular Fractures", Hospital for Special Surgery, Mar. 30, 2006, HSS.edu, Mar. 30, 2006, pp. 1-9.
Novick, "Pelvic Fractures/Acetabular Fractures—An Interview with Dr. David L. Helfet", Hospital for Special Surgery, accessed at http://www.hss.edu/conditions—pelvic-acetabulum-fractures.asp, Mar. 30, 2006, 10 Pages.
Starr, "Fractures of the Pelvic Ring", in Rockwood & Green's Fractures in Adults 6th Edition, Chapter-41, accessed on Feb. 4, 2014, Lippincott Williams & Wilkins, pp. 1-40.
Starr et al., "Superior Pubic Ramus Fractures Fixed With Percutaneous Screws: What Predicts Fixation Failure?", Journal of Orthopaedic Trauma, vol. 22, No. 2, Lippincott Williams and Wilkins, Feb. 2008, pp. 81-87.
Vaidya, R., et al., "Complications of Anterior Subcutaneous Internal Fixation for Unstable Pelvis Fractures: A Multicenter Study", Clinical Orthopaedics and Related Research, vol. 470, No. 8, Springer, Aug. 2012, pp. 1-8.
U.S. Patent and Trademark Office, "Office Action", U.S. Appl. No. 16/340,067, dated Oct. 4, 2021, pp. 1 Through 97, Published: US.

\* cited by examiner

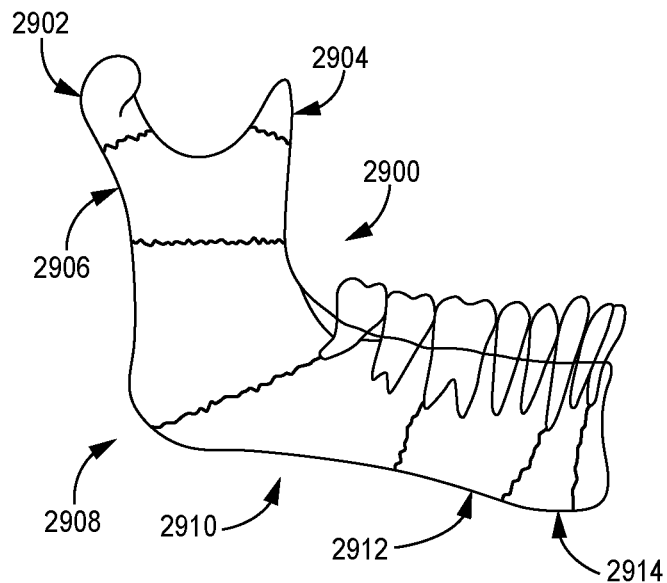
FIG. 28
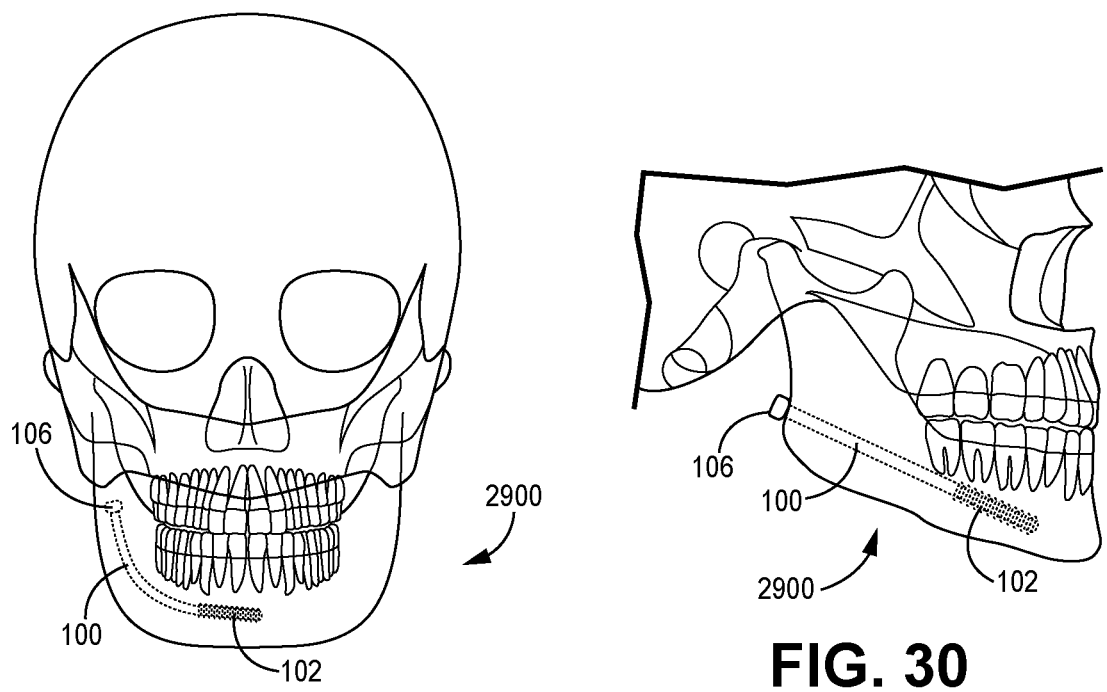
FIG. 29
FIG. 30

BONE-FIXATION DEVICE AND SYSTEM

This application claims priority to International Patent Application No. PCT/CA2019/051471 filed on Oct. 17, 2019.

RELATED AND PRIORITY APPLICATIONS

This patent application claims priority to: U.S. Provisional Patent Application Ser. No. 62/747,039, which is titled USE OF RODSCREW IN MEDICAL APPLICATIONS OTHER THAN TREATING A FRACTURE OF THE PELVIS, and which was filed 17 Oct. 2018; and U.S. Provisional Patent Application Ser. No. 62/905,925, which is titled BONE-FIXATION DEVICE AND SYSTEM, and which was filed 25 Sep. 2019. The afore-mentioned provisional patent applications are incorporated herein by reference.

SUMMARY

The following publications describe using a rodscrew, such as the one of the rodscrews described below in conjunction with FIGS. 1 and 3-5, for fixating one or more pelvic fractures, and are incorporated herein by reference: U.S. Pat. No. 9,839,435; US 2017/0020585; US 2017/0238977; PCT/US2017/055442; WO 2018/067888; WO 2013/071432; U.S. Pat. No. 9,498,264; US 2017/0238977; U.S. Provisional Patent Application Ser. No. 62/747,101, which is titled INTRAMEDULLARY DEVICE and which was filed 17 Oct. 2018; and U.S. Provisional Patent Application Ser. No. 62/906,048, which is titled INTRAMEDULLARY FIXATION DEVICE and which was filed 25 Sep. 2019.

But such a rodscrew can be configured, and can be used, to fixate, or otherwise to treat, fractures of bones other than the pelvis, and can be configured, and can be used, for purposes other than fracture fixation, such other purposes including, but not limited to, treating maladies such as scoliosis, and securing an implanted device, such as a prosthetic, to tissue such as bone.

An embodiment of a rodscrew, such as for use in the treatments and procedures described above and below, includes at least two internal cables, but often includes three, four, or more cables for added stability and the ability to lock into any curved shape that the rodscrew can attain while in its flexible configuration, mode, or state.

Furthermore, an embodiment of the rodscrew can have a width that tapers along its length to correspond to the taper in the width of a bone, or a series of bones such as the spine (series of vertebrae), the width of which decreases as one moves toward the coccyx from the $1^{st}$ sacral vertebra (S1) and also decreases as one moves up the vertebral column to the neck.

Moreover, an embodiment of the rodscrew can have a respective anti-infection coating, such as silver, which has anti-bacterial properties, or such as diamond, which presents a low-friction surface that is so smooth that it may prevent formation of a biofilm that can give rise to infection.

In addition, an embodiment of a bone-fracture fixation device, such as a rodscrew, includes a flexible body, a plurality of flexible members, and first and second interfaces. The flexible members are disposed longitudinally within the flexible body, such that the flexible body is rigid when the flexible members are fixed into position. And the first and second interfaces are respectively coupled to the flexible body, each of at least one of the first and second interfaces including a respective at least one hole each configured to receive a respective attachment member configured to engage a bone. An example of such an attachment member is a locking screw.

BRIEF DESCRIPTION OF THE DRAWINGS

FIG. 28 is a side view of a human mandible including multiple fractures.

FIGS. 29-30 are front and side views, respectively, of a human mandible having implanted therein at least one rodscrew of FIG. 1, 5, or 6 to fixate at least one mandible fracture, according to an embodiment.

DETAILED DESCRIPTION

Each value, quantity, or attribute herein preceded by "substantially," "approximately," "about," a form or derivative thereof, or a similar term, encompasses a range that includes the value, quantity, or attribute ±20% of the value, quantity, or attribute, or a range that includes ±20% of a maximum difference from the value, quantity, or attribute, or ±20% of the difference between the range endpoints. For example, an "approximate" range of b-c is a range of b−20%·(c−b) to c+20%·(c−b). Furthermore, the terms "a," "an," and "the" can indicate one or more than one of the objects that they modify.

Figure 1:
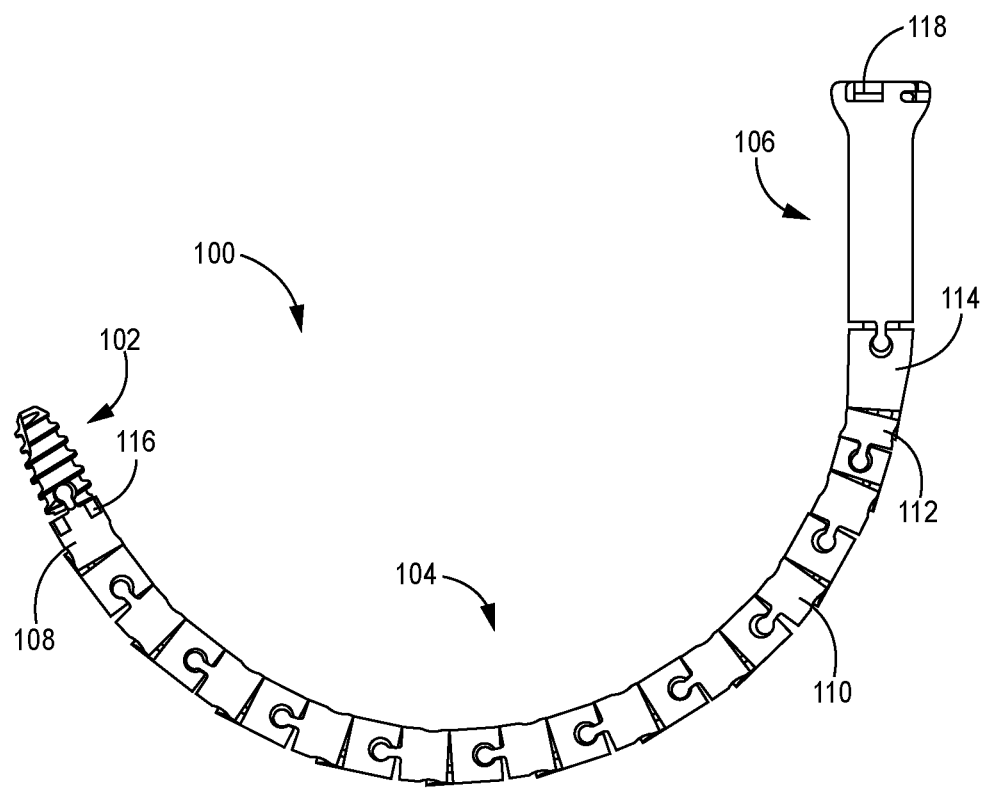
FIG. 1 is a plan view of a rodscrew in a curved configuration, according to an embodiment.

FIG. 1 is a plan view of a rodscrew 100, which is configured to fixate a bone fracture (not shown in FIG. 1), is flexible in an unlocked configuration (also called an unlocked state or an unlocked mode), and is rigid in a curved or straight shape in a locked configuration (also called a locked state or a locked mode), according to an embodiment. For example, the rodscrew 100 may be similar to one or more of the rodscrews described in U.S. Provisional Patent Application Ser. No. 62/747,101, and may have one or more features similar to the features described in WO 2018/067888.

The rodscrew 100 includes a distal end 102 (also called a distal segment) 102, a body 104, which is configurable in flexible and rigid configurations, and a proximal end 106 (also called a proximal segment).

The distal end 102 is attached to, and is tapered in a direction away from, the body 104, and is threaded for engagement with a tissue such as bone (not shown in FIG. 1) to secure the implanted rodscrew 100 in a desired position and in a desired shape (e.g., a shape with one or more bends or curves) within an intramedullary space of the bone.

The body 104 is formed from a number of different types of beads (also called segments), including an anchor bead 108, main-body beads 110, an optional one or more spacer beads 112, and a transition bead 114. The anchor bead 108 is configured to anchor distal ends 116 of the cables (described below in conjunction with FIG. 3) that extend within the beads 108, 110, 112, and 114 from the proximal end 106 to the distal end 102, and is configured to couple the distal end 102 to the body 104. The main-body beads 110 are configured to allow the rodscrew 100 to flex into one or more curved configurations while in an unlocked state. The one or more spacer beads 112 are configured to allow one to configure the rodscrew 100 to have a length suitable for a particular application. For example, a rodscrew 100 suitable for fixating a pelvic fracture may be longer than a rodscrew suitable for fixating a rib fracture or a clavicle fracture. And the transition bead 114 is configured to couple the proximal end 106 to the body 104.

The proximal end 106 includes an engagement end 118 configured to receive a tool for rotating the rodscrew 100, for example to "screw" the distal end 102 into bone, for hammering the rodscrew in circumstances where rotation is unsuitable, and for transitioning the rodscrew between unlocked and locked configurations.

During an embodiment of an implant procedure, a medical professional, such as an orthopedic surgeon, inserts a guidewire (not shown in FIG. 1) into the intramedullary space of a fractured bone, such that the guidewire spans the fracture(s). The guidewire may include a bent ball tip to facilitate steering, or may have a straight end.

Next, the surgeon guides a first reaming tool over the guidewire to ream a path wide enough to accommodate the distal end 102, main body 104, and all but the engagement end 118.

Then, the surgeon removes the first reaming tool.

Next, the surgeon guides a second, wider reaming tool over the guidewire and reams the path almost, but not quite, to the end of the original path to effectively form a path extension that is narrower than the remaining portion of the reamed path; the path extension is narrow enough to accommodate the threads of the distal end 102 so that the surgeon can secure the rodscrew 100 to bone by screwing the distal end into the path extension.

Then, the surgeon places a flexible exchange tube over the path-forming guidewire (surgeon, exchange tube, and guidewire not shown in FIG. 1), removes the guidewire, and inserts, in the guidewire's place, a driving guidewire (not shown in FIG. 1).

Then, the surgeon unlocks the rodscrew 100 if the rodscrew is not already unlocked.

Next, the surgeon inserts the unlocked, and, therefore, flexible, rodscrew 100 over the guidewire (the rodscrew has a central bore, not visible in FIG. 1, configured to receive the guidewire so that the rodscrew can slide over the guidewire) and through the reamed path such that the flexible rodscrew assumes the shape (e.g., straight, curved) of the path.

Then, the surgeon secures the rodscrew 100 to the bone by, for example, rotating the rodscrew such that the threads of the distal end 102 screw into, and, therefore, engage, the path extension.

When the rodscrew 100 is fully implanted, only the engagement end 118 protrudes from the path in the fractured bone.

Next, the surgeon removes the guidewire.

Then, the surgeon transitions the rodscrew 100 from an unlocked configuration to a locked configuration such that the rodscrew rigidly retains the shape that it has acquired, whether the shape is curved or straight.

Because the locked rodscrew 100 is rigid, it can support loads associated with normal movement of the bone, and, therefore, can maintain fixation of the sections of the fractured bone so that the fracture heals properly.

Alternate embodiments of the rodscrew 100, and of the described procedure for implanting the rodscrew, are contemplated. For example, the rodscrew 100 can have a width that tapers along its length to correspond to the taper in the width of a bone, or of a series of bones such as the spine (series of vertebrae), the width of which decreases as one moves toward the coccyx from the $1^{st}$ sacral vertebra (S1) and also decreases as one moves up the vertebral column from the sacral vertebrae to the neck. Furthermore, the rodscrew 100 can have a respective anti-infection coating, such as silver, which has anti-bacterial properties, or such as diamond, which presents a low-friction surface that is so smooth that it may prevent formation of a biofilm that can give rise to infection. Moreover, one may use respective guidewires for different steps of the rodscrew implant procedure. In addition, one or more embodiments described in conjunction with FIGS. 2-42 may be applicable to the rodscrew 100 or to a procedure for implanting the rodscrew.

Figure 2:
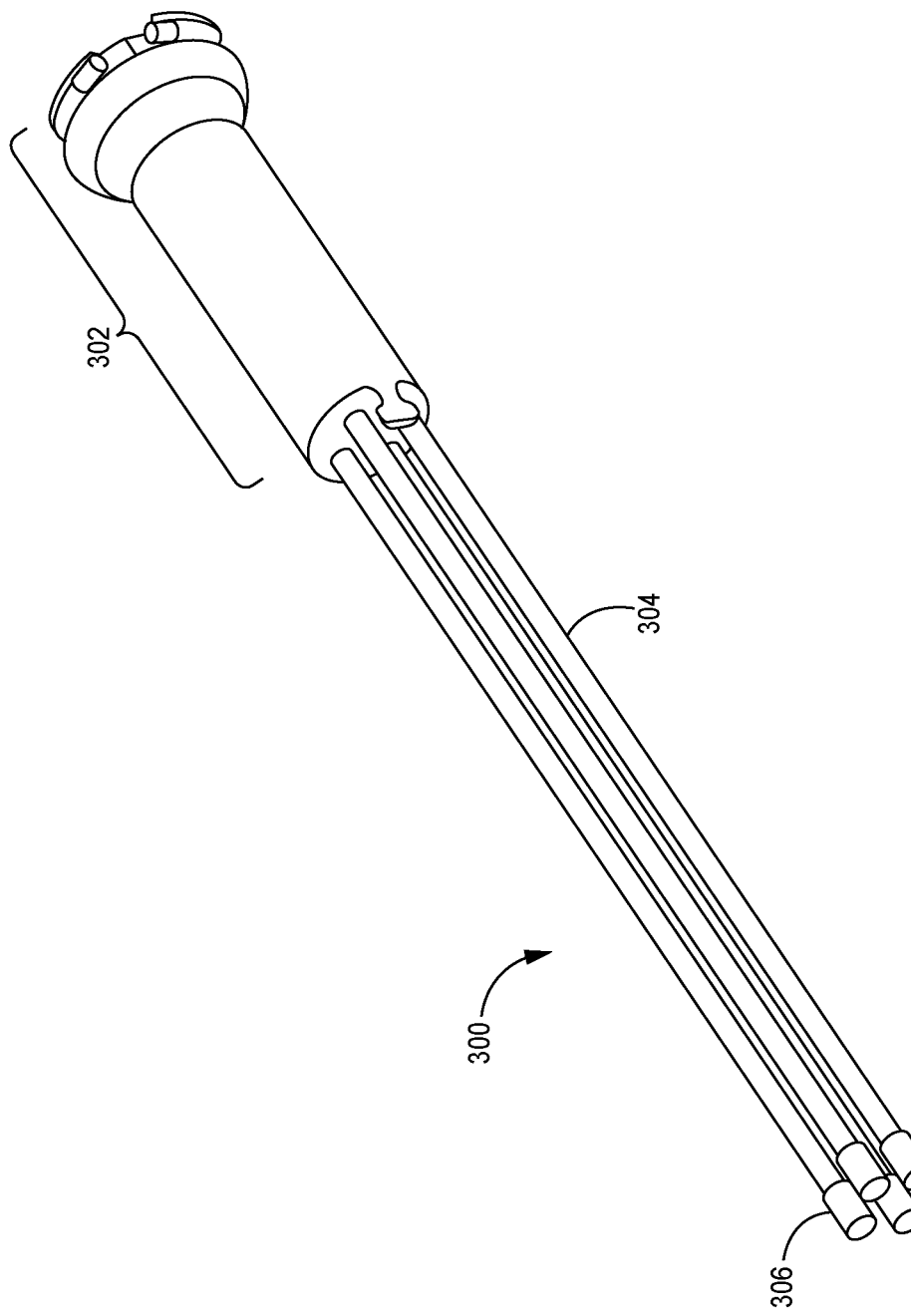
FIG. 2 is an isometric view of the rodscrew of FIG. 1 in a straight configuration with the body segments and distal end omitted, according to an embodiment.

FIG. 2 is an isometric view of a rodscrew 300 with the beads of the main body and the distal end omitted, according to an embodiment. The rodscrew 300 can be the same as, or similar to, the rodscrew 100 of FIG. 1.

In addition to a proximal end 302, which can be the same as, or similar to, the proximal end 106 of FIG. 1, the rodscrew 300 includes cables, for example, four cables, 304, each of which extends from the proximal end, through a respective cable bore of each of the beads (not shown in FIG. 2) that form a body of the rodscrew, to an anchor bead (not shown in FIG. 2 but can be similar to the anchor bead 108 of FIG. 1).

And each of the cables 304 includes, at its distal end, a respective cable cap 306, which can be compression fitted onto the end of the cable. The cable cap 306 engages a respective cable slot in the anchor bead, for example, as shown in conjunction with the anchor bead 108 and cable ends 116 of FIG. 1.

The cables 304 are, at least ideally, of equal length, and are flexible. For example, each cable may be formed from strands of a metal such as steel. The cables 304, also called flexible members, extend from the last anchor bead 108 to, and into, the proximal end 106. The flexible members can also be metal wires, fibers, plastic or other fibers (e.g., carbon fiber) in construction.

While the rodscrew 300 is unlocked, the cables 304 are able to slide past one another in response to a bending of the rodscrew.

And, while the rodscrew 300 is in a curved configuration, at least one of the cables 304 has a slightly different bend radius than at least one other of the cables, and cables with different bend radii each have a slightly different linear length between two arbitrary points along the body of the rodscrew.

While the rodscrew 300 is locked, positions of the cables 304 relative to one another are fixed such that the cables are unable to slide past one another.

Therefore, locking the rodscrew 300 while in a curved configuration causes the rodscrew to be rigid (unflexible) yet to retain a curved shape by fixing the relative positions, and, therefore the bend radii, of the cables 304.

Alternate embodiments of the rodscrew 300 are contemplated. For example, one or more embodiments described in conjunction with FIGS. 1 and 4-42 may be applicable to the rodscrew 300.

Figure 3:
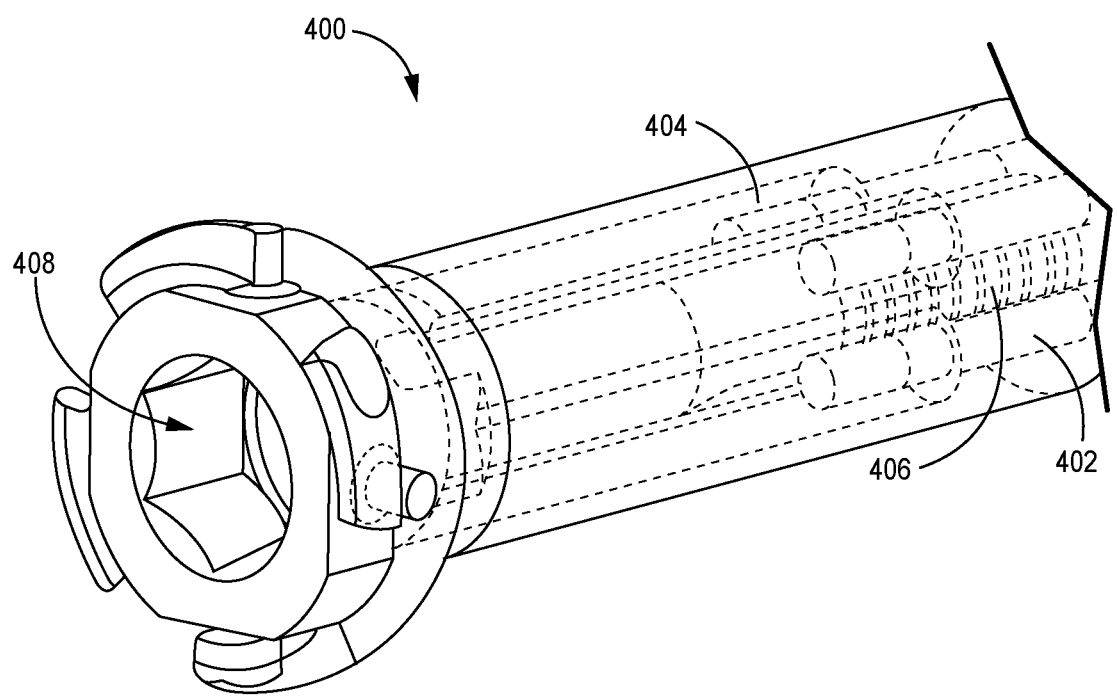
FIG. 3 is a transparent view of the proximal end of one of the rodscrews of FIGS. 1-2 in an unlocked configuration, according to an embodiment.

FIG. 3 is a transparent view of a proximal end 400 while in an unlocked configuration, the proximal end being the same as, or similar to, one or more of the proximal ends 104 and 302 of FIGS. 1-2, respectively, according to an embodiment. The proximal end 400 also can be the same as, or similar to, the proximal end described in WO 2018/067888.

The proximal end 400 is configured to receive cables 402 within cable slots 404, and includes a cam 406 coupled to an engagement receptacle 408.

While the proximal end 400 is in an unlocked configuration, the cam 406 is oriented such that the cables 402, which may be similar to the cables 304 of FIG. 2, are free to slide within the cable slots 404, and, therefore, are free to slide relative to one another.

Figure 4:
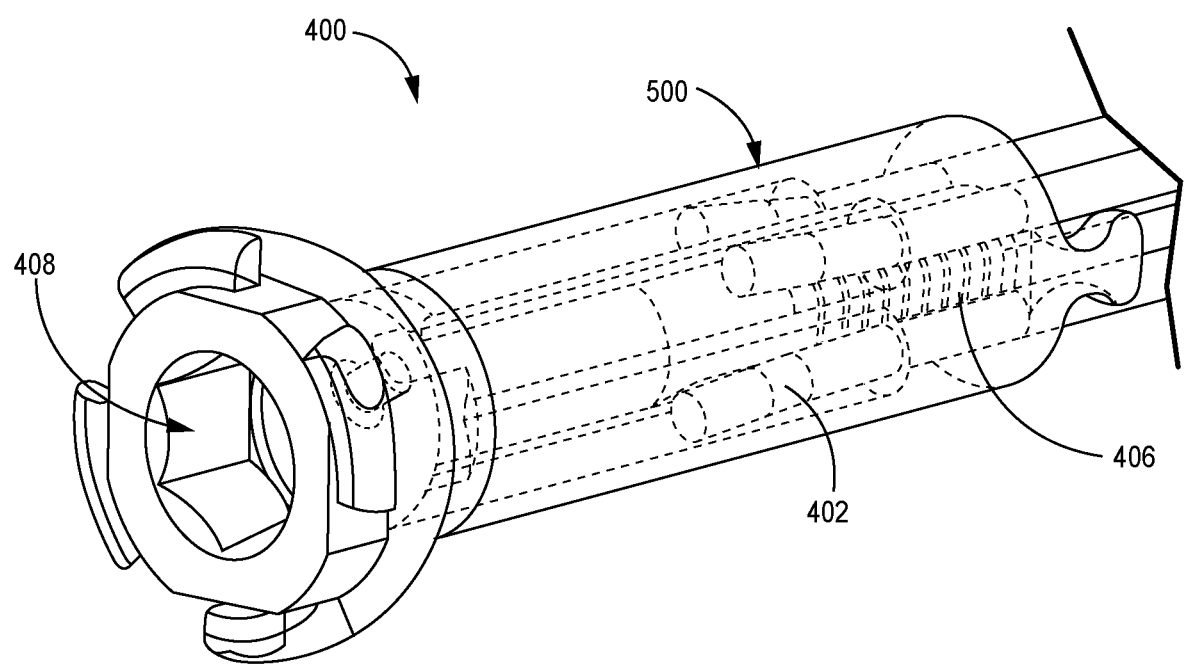
FIG. 4 is a transparent view of the proximal end of FIG. 3 in a locked configuration, according to an embodiment.

FIG. 4 is a transparent view of the proximal end 400 of FIG. 3 while in a locked configuration, according to an embodiment.

While the proximal end 400 is in a locked configuration, the cam 406 is oriented such that the cam compresses the cables 402 against the inner wall(s) of a housing of the proximal end 400 such that the cables are not free to slide relative to one another, and, therefore, are in respective fixed positions relative to each other.

Referring to FIGS. 3-4, operation of the proximal end 400 is described, according to an embodiment.

To transition the proximal end 400 from an unlocked configuration (FIG. 3) to a locked configuration (FIG. 4), one inserts a tool (e.g., a hexagonal wrench, not shown in FIGS. 3-4) into the receptacle 408 and rotates the cam 406 clockwise until the cam engages the cables 402 and compresses them against the inner wall(s) of the housing 500.

And to transition the proximal end 400 from a locked configuration (FIG. 4) to an unlocked configuration (FIG. 3), one inserts a tool (e.g., a hexagonal wrench, not shown in FIGS. 3-4) into the receptacle 408 and rotates the cam 406 counterclockwise until the cam disengages and releases the cables 402 such that the cables are no longer compressed against the inner wall(s) of the housing 500.

Still referring to FIGS. 3-4, alternate embodiments of the rodscrew proximal end 400 are contemplated. For example, one or more embodiments described in conjunction with FIGS. 1-2 and 5-42 may be applicable to the proximal end 400.

Figure 5:
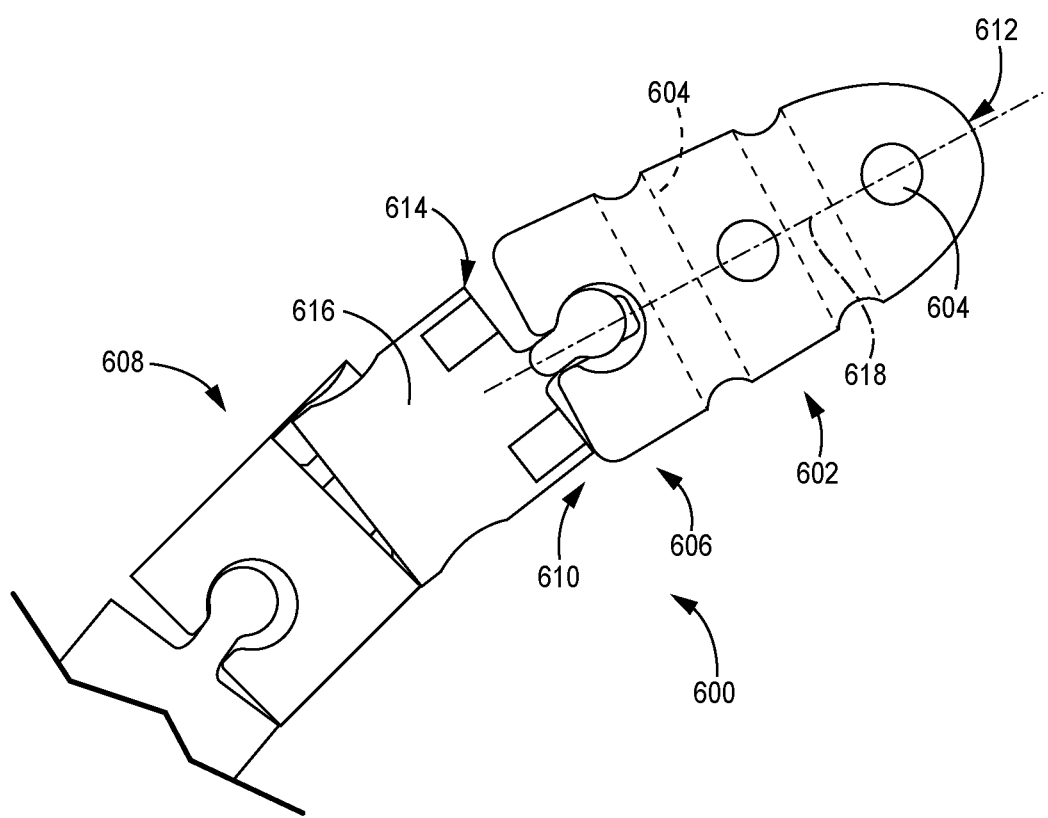
FIG. 5 is a side view of a portion of a rodscrew that is similar to the rodscrews of FIGS. 1-2 but that has a distal end configured for receiving screws, according to an embodiment.

FIG. 5 is a side view of a distal portion of a rodscrew 600, which can be similar to the rodscrew 100 of FIG. 1, respectively, except that a distal end 602 may or may not include cancellous or cortical bone threads, and includes one or more locking screw holes 604 each configured to receive an attachment member. For example, a locking screw attachment member (not shown in FIG. 5), according to an embodiment. Each of the one or more holes 604 can have any suitable orientation relative to the other holes. For example, one locking screw hole 604 can be orthogonal to one or more of the other locking screw holes. Alternatively, for example, the locking screw hole could be spaced at 45°, 60°, or 90° increments circumferentially around the rodscrew from the first set of holes at the same position along the rodscrew length. Furthermore, a locking screw hole 604 configured to receive a locking screw may be threaded.

The distal end 602 is, at its widest part 606, as wide as, or wider than, a rodscrew body 608, and is tapered inward from a trailing side 610 (the trailing side is also the widest part in the described embodiment) to a leading side 612.

During an embodiment of a procedure for implanting the rodscrew 600, a surgeon reams a path through an intramedullary space within a fractured bone, hammers the rodscrew (e.g., over a guidewire disposed within the path) into the path, and secures the distal end 602 to the bone by inserting a respective locking screw (locking screws not shown in FIG. 5) through each of one or more of the holes 604 and by rotating each screw through the selected lock screw holes into the bone. The taper of the distal end 602 facilitates the insertion, by hammering, of the rodscrew 600 into the reamed path. And because the widest part 606 of the distal end 602 is at least as wide as the rodscrew body 608, a leading side 614 of an anchor bead 616 is less likely to "catch" on a side wall of the reamed path.

Alternate embodiments of the rodscrew 600 are contemplated. For example, each of one or more of the locking screw holes 604 may be oriented at other than a right angle or other angle relative to a longitudinal axis 618 of the distal end 602. Furthermore, one or more embodiments described in conjunction with FIGS. 1-4 and 6-42 may be applicable to the rodscrew 600.

Figure 6:
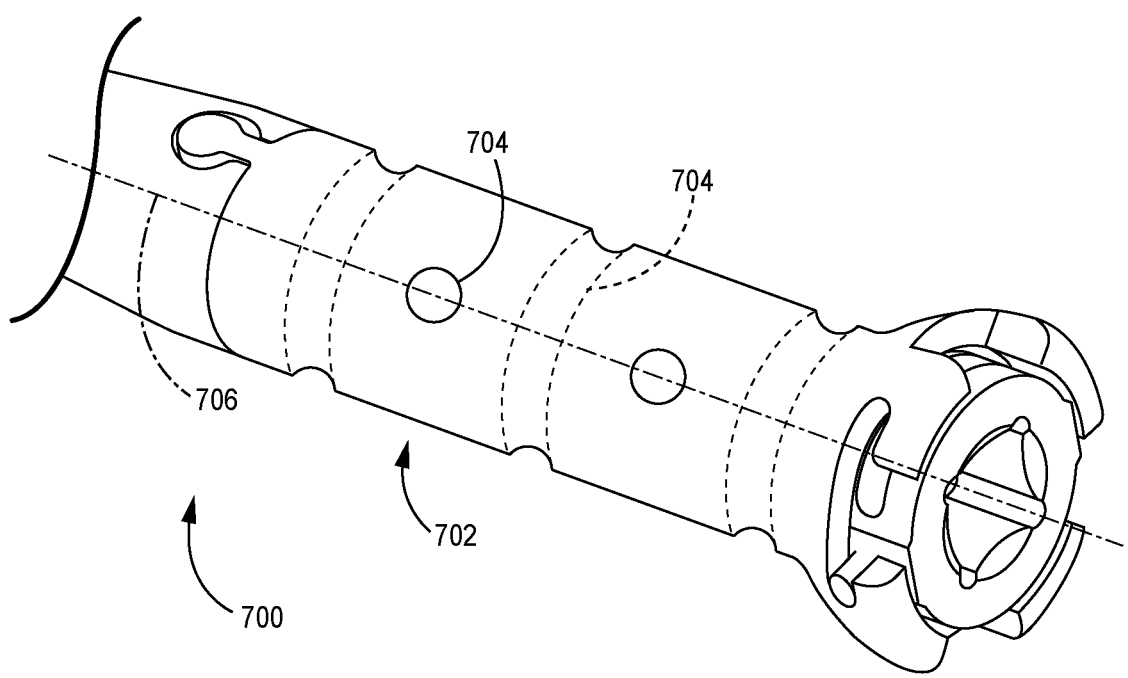
FIG. 6 is a side view of a portion of a rodscrew that is similar to the rodscrews of FIGS. 1-2 but that has a proximal end configured for receiving screws, according to an embodiment.

FIG. 6 is a side view of a proximal portion of a rodscrew 700, which can be similar to the rodscrews 100 and 600 of FIGS. 1 and 6, respectively, except that a proximal end 702 includes one or more locking screw holes 704 each configured to receive a locking screw (not shown in FIG. 6), according to an embodiment. Each of the one or more holes 704 can have any suitable orientation relative to the other holes. For example, one locking screw hole 704 can be orthogonal or at another angle to one or more of the other locking screw holes. Furthermore, a locking screw hole 704 configured to receive a locking screw may be threaded or may have a smooth wall.

During an embodiment of a procedure for implanting the rodscrew 700, a surgeon reams a path through an intramedullary space within a fractured bone, hammers the rodscrew (e.g., over a guidewire disposed within the path) into the path, and secures the proximal end 702 to the bone by inserting a respective locking screw (locking screws not shown in FIG. 6) through each of one or more of the holes 704 and by rotating each screw, into the bone.

Alternate embodiments of the rodscrew 700 are contemplated. For example, each of one or more of the locking screw holes 704 may be oriented at other than a right angle relative to a longitudinal axis 706 of the proximal end 702. Furthermore, one or more embodiments described in conjunction with FIGS. 1-5 and 7-42 may be applicable to the rodscrew 700.

Procedures and Treatments Using One or More of the Rodscrews

As described below in conjunction with FIGS. 7-42, a medical professional, such as an orthopedic surgeon, can use one or more of the rodscrews 100, 600, and 700 of FIGS. 1, 5, and 6, respectively, and embodiments thereof, in procedures for, or otherwise corresponding to, the treatment of each of at least the following conditions and maladies:
(1) Conditions of, and procedures for, the spine, such as spinal fusion, scoliosis, kyphosis, and kyphoscoliosis.
(2) Fractures of the proximal femur.
(3) Total hip replacement.
(4) Fractures of the proximal humerus and the distal humerus.
(5) Fractures of the radius and ulna.
(6) Fractures of the clavicle.
(7) Separations of the Acromioclavicular (AC) joint.
(8) Fractures of the mandible (lower jaw).
(9) Fractures of the calcaneus (heel bone).
(10) Fractures of the ribs.
(11) Fractures of bones in adolescents who are still growing, such bones including, but not limited to, the "long bones" (femur, tibia, fibula) in the leg and (humerus, radius, ulna) in the arm.

Figure 7:
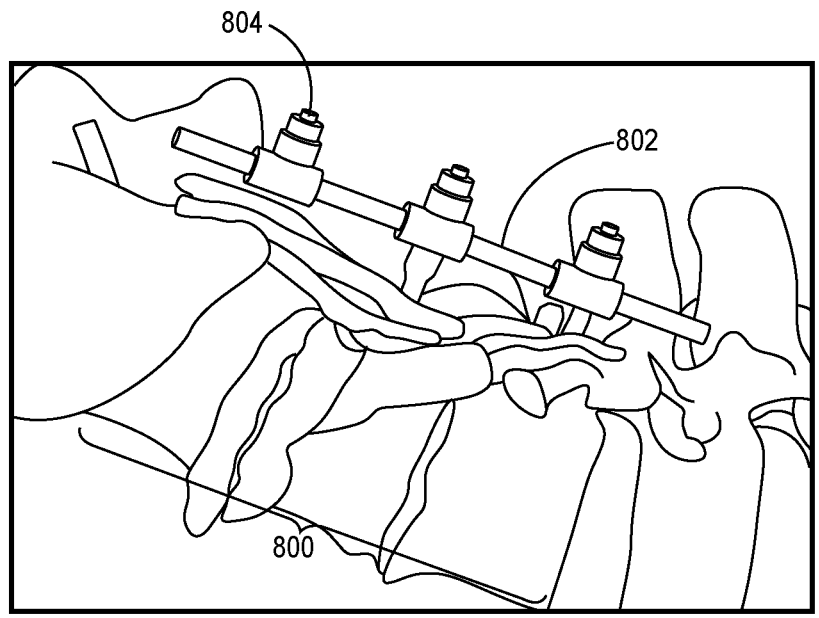
FIGS. 7-8 are a respective side view and an x-ray view of fused vertebrae stabilized with rods and pedicle screws.
Figure 8:
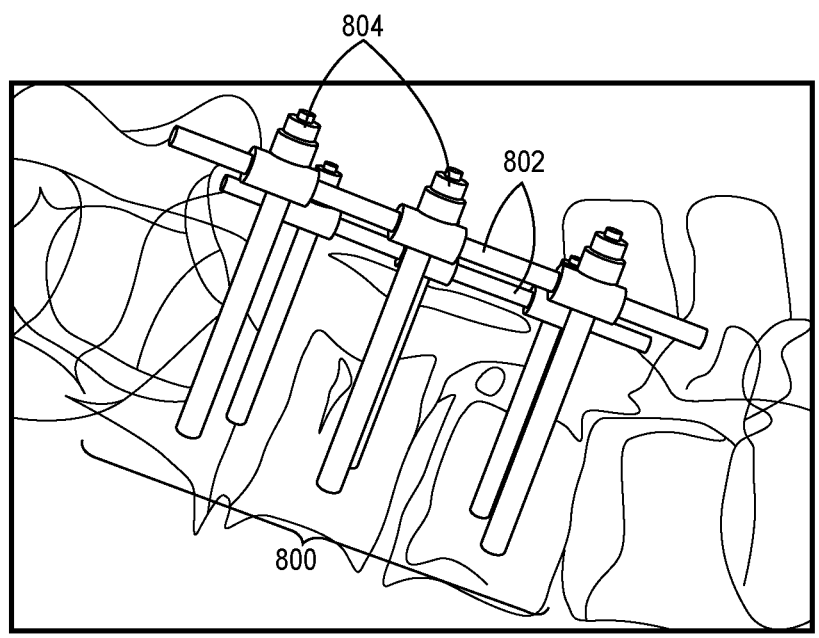

Using a Rodscrew to Treat Conditions of, and in Procedures Related to, the Spine Spinal Fusion FIG. 7 is a side view of fused human vertebrae 800 conventionally stabilized with conventional rods 802 and conventional pedicle screws 804, and FIG. 8 is an x-ray of the spine section of FIG. 7.

A normal human spine has a natural curvature in which the radii of the spinal curves extend in the sagittal (front/back) plane. That is, if one could view a normal spine from directly in front of, or from directly behind, a human, the normal spine would appear to be straight, and if one could view a normal spine from either side of a human, the normal spine would appear to have a curved, S-like shape.

Spinal fusion is the fusing together of two or more immediately adjacent vertebra 800 and is typically performed in subjects in whom the segment or segments (e.g., vertebra or vertebrae 800) of the spine are unstable from a variety of causes. The instability can cause, or causes, pain, paralysis, or both pain and paralysis. Causes of such an instability include degenerative changes of old age, injuries (fractures and dislocations), and a variety of developmental spinal conditions.

During a conventional spinal-fusion procedure for a pair of vertebrae 800, a surgeon first exposes the portion of the spine containing the damaged disc between the pair of vertebrae through the back side of the subject, and "cleans out" the region between the two vertebrae. This "cleaning out" entails removing all pieces of the damaged disc and removing pieces of bone for access (e.g. spinous process).

Next, the surgeon forms a bone graft between the two vertebrae 800 with bone material from another of the subject's bones, or from a cadaver.

Then, the surgeon stabilizes the unstable segment or segments of the spine using some type of implant. Quite commonly, this implant is a series of pedicle screws 804 fixed with posterior rods 802. Pedicle screws 804 act a bit like a bumper jack and hold the anterior (front) of the vertebrae 800 apart.

Unfortunately, the normal compressive forces (e.g., due to movement or position of the subject) that press together the front edges of the vertebrae 800 can cause a pedicle screw 804, or another type of implant, to fail. A pedicle screw 804 itself can fail, the implant can fail at the junctions of the pedicle screws with the posterior rod 802, or the posterior rod could bend or break. Failure of the implant can lead to instability or continuous movement between the vertebrae 800 being fused. If there is motion, the bone will not heal (i.e., will not incorporate the bone graft between the vertebrae 800).

But using one or more flexible rodscrews, such as the rodscrews 100, 600, and 700 of FIGS. 1, 5, and 6 (which rodscrews can be made rigid after implantation), along, or in combination, with, for example, a tension band or other device on the posterior parts of one or more vertebrae 800 can take the place of pedicle screws 804 fixed with posterior rods 802 or other spinal-fusion devices and can prevent or minimize failures due to compressive forces. For purposes of example, use of only the rodscrew 100 of FIG. 1 is described hereinafter, it being understood that one or more of the other rodscrews 600 and 700, or any other similar rodscrew, can be used in a similar manner.

For example, referring to FIGS. 1, 7, and 8, with a spinal-device configuration with a tension band or rods on the posterior parts of the vertebra 800 (for example, the tension band could be across the either transverse process, spinous process, and/or lamina, or, for example, across pedicle screws/rods where the pedicle screws are shorter in length than as shown in FIGS. 7 and 8) similar to a chain from the ground into one end of a seesaw and then using the rodscrew as an anti-compressive device in the front (similar to putting a solid block between the ground and the other end of the seesaw.)

Moreover, because the human spine tapers in width from bottom (wider) to top (narrower), the rodscrew 100 can be constructed also to taper in width from its distal end 102 (narrower) to its proximal end 106 (wider). Alternatively, the rodscrew 100 can be constructed to taper in width from its proximal end 106 (narrower) to its distal end 102 (wider) if the rodscrew is configured to be inserted at an upper location of the spine and to extend toward a lower location of the spine.

Figure 9:
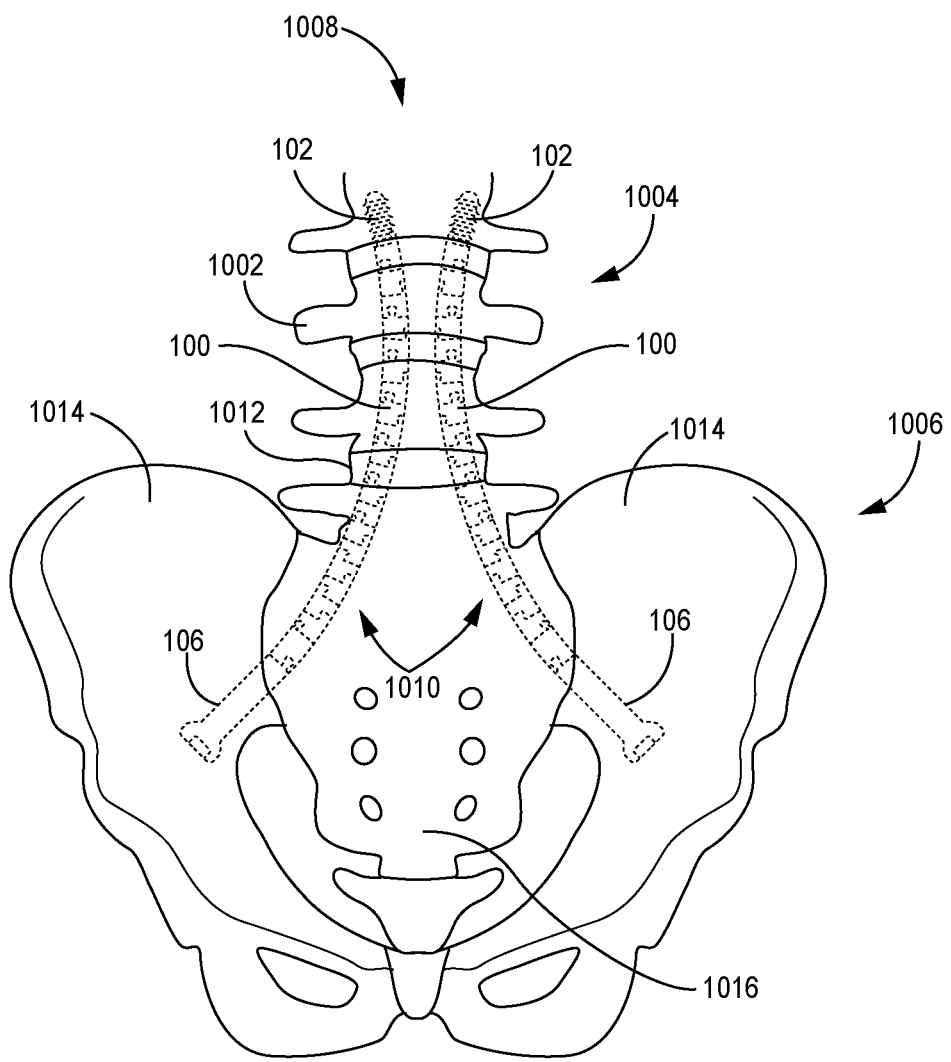
FIGS. 9-10 are front and transverse views, respectively, of fused human vertebrae stabilized with one or more the rodscrews of FIG. 1, 5, or 6, according to an embodiment.
Figure 10:
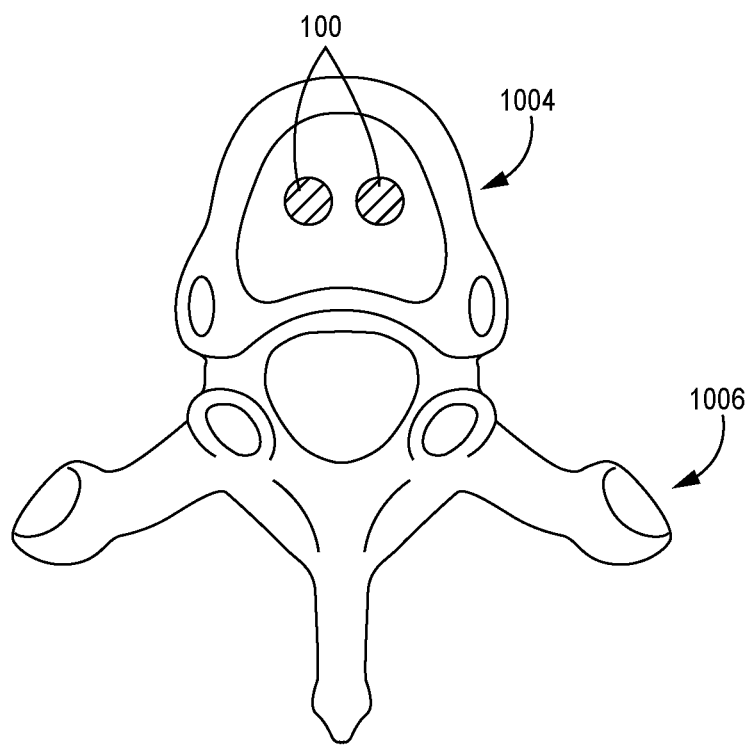

FIGS. 9-10 are front and transverse views, respectively, of fused human vertebrae 1002 stabilized with one or more rodscrews 100, 600, or 700 of FIGS. 1, 5, and 6, respectively, according to an embodiment. For purposes of example, use of the rodscrew 100 of FIG. 1 is described hereinafter, it being understood that any of the other rodscrews 600 and 700, or any other similar rodscrew, may be used in a similar manner.

Described in conjunction with FIGS. 1, 9, and 10 is an embodiment of a procedure for implanting one or more rodscrews 100 into a region 1004 of an adult human spine to stabilize the region as part of spine-fusing procedure. Each rodscrew 100 enters through the pelvis 1006 and each distal screw end 102 is embedded into a vertebral body 1008.

Rodscrew fixation may be useful with fixation of the lumbar vertebrae, sacral vertebrae, or both the lumbar and sacral vertebrae where access through the pelvis 1006 may reduce invasiveness of the fixation procedure.

Described below is an embodiment of a procedure for implanting one rodscrew 100, it being understood that the procedure for implanting each of one or more rodscrews may be similar.

First, a surgeon (not shown in FIGS. 9-10) exposes a portion of the pelvis 1006 through the skin, subdermal fat, and the gluteus maximus muscle (none of these tissues shown in FIGS. 9-10), and then drills a hole (not shown in FIGS. 9-10) into the exposed portion of the bone (e.g., a portion of the left or right ilium 1014 or a portion of the sacrum 1016) of the pelvis.

Next, the surgeon inserts a steerable guidewire (neither surgeon nor guidewire shown in FIGS. 9-10) into the hole (not shown in FIGS. 9-10), the guidewire having a sharp, bent leading end. The sharp, bent end allows the surgeon to manipulate and direct the guide wire to form an implantation pathway 1010 through the intramedullary spaces of the bone(s) of the pelvis 1006 and through one or more vertebrae 1002. The pathway 1010 may be curved, and the surgeon can form the curved pathway with a series of alternating forward motion (e.g., hammering) and of turning the guidewire's bent tip.

Then, the surgeon guides the steerable guidewire (neither surgeon nor guidewire shown in FIGS. 9-10) across one or more intervertebral discs 1012 and vertebral bodies (a vertebral body is a portion of a vertebra 1002) in a generally superior (i.e., towards the subject's head) direction by a conventional guiding technique such as two- or three-dimensional fluoroscopic imaging.

Next, the surgeon inserts, over the path-forming guidewire, a flexible reamer (surgeon, guidewire, and reamer not shown in FIGS. 9-10) and reams the pathway 1010, which, in the described example, is a curved pathway.

The guidewire may also have a small ball (not shown in FIGS. 9-10) permanently attached to it at or near its leading end to assure removal of the reamer tip in the event of reamer breakage.

Then, the surgeon places a flexible exchange tube over the path-forming guidewire (surgeon, exchange tube, and guidewire not shown in FIGS. 9-10), removes the guidewire, and inserts, in the guidewire's place, a driving guidewire (not shown in FIGS. 9-10).

Next, the surgeon (not shown in FIGS. 9-10) inserts the unlocked, and, therefore, flexible, rodscrew 100 over the driving guidewire (the rodscrew has a central bore configured to receive the guidewire such that the surgeon can slide the rodscrew over the guidewire).

Then, the surgeon uses a tool (neither surgeon nor tool shown in FIGS. 9-10) to rotate the rodscrew 100 such that a threaded distal end 102 of the rodscrew "screws into," or otherwise engages, a bone structure, such as the top of the body of the last vertebra 1002 in the chain of vertebrae into which the rodscrew extends.

At the same time, the proximal end 106 of the rodscrew 100 engages the entry hole (not shown in FIGS. 9-10) in a pelvic bone (e.g., the ilium 1014 or the sacrum 1016) of the pelvis 1006. The portion of the proximal end 106 of the rodscrew 100 that engages with the pelvic bone may include a flange, thread, or separator washer (neither flange, thread, or washer shown in FIG. 9) to enhance the engagement of the proximal end with the bone forming the entry hole and to provide a stop configured to limit how far the surgeon can insert the proximal end into the entry hole.

Alternatively, the distal end 102 of the rodscrew 100 may not be threaded (like the distal end 602 of FIG. 5), and the surgeon may use a tool (neither surgeon nor hammer shown in FIGS. 9-10) to hammer the distal end into a bone structure, such as the top of the body of the last vertebra 1002 in the chain of vertebrae through which the rodscrew extends.

After the proximal and distal ends 106 and 102 of the rodscrew 100 are secured to bone, the rodscrew, still in its flexible state, has a shape that follows the contours of the formed path 1010. Because the formed path 1010 typically has one or more curves or bends, the flexible rodscrew 100 typically has the curved or bent shape that the rodscrew has assumed from the path; that is, the flexible rodscrew typically has the same shape as the path.

Next, the surgeon (not shown in FIGS. 9-10) transitions the rodscrew 100 from its flexible state to its rigid state to lock the rodscrew into the shape that the rodscrew has assumed post implantation. As described above, the shape of the rodscrew 100 is typically the shape of the path 1010, which typically includes at least one curve or bend.

While locked into its rigid shape, the rodscrew 100 is configured to bear at least portions of the compressive, bending, and tensile loads that the fused region 1004 of the spine experiences during the healing process.

Alternative embodiments of the above-described spine-fusion procedure are contemplated. For example, a surgeon can implant multiple rodscrews 100 to stabilize the spine. Furthermore, once the fusion graft(s) is(are) healed, a surgeon can remove the rodscrew(s) 100, or the rodscrew(s) can remain implanted. To facilitate removal of a rodscrew 100 if a proximal end 106 of the rodscrew is accessible from the outside of the pelvic bone, the surgeon can perform a skin incision and accesses the rodscrew proximal end both to unlock the rodscrew to convert it into a flexible state (so that the rodscrew can flex as needed during the removal) and to grasp the rodscrew to unscrew it, or otherwise to pull it, from the bone and, ultimately, to remove the rodscrew from the path 1010.

Still referring to FIGS. 9-10, a spinal-fusion cage (not shown in FIGS. 9-10) may not be needed. With the rodscrew 100, the bone graft would be inserted posteriorly through the pedicles. All the soft tissues around the outside of the disc space would be intact and would hold the bone graft in place. When a cage is used it typically has two functions: 1) the cage acts as a spacer (anterior jack), and (2) holds the bone graft in place. The cage may be needed to hold the bone graft in place because the procedure of putting the cage in necessarily removes the ligaments around the disc so that the ligaments are no longer available to hold the bone graft in place.

Moreover, a surgeon can implant a rodscrew 100 per above as part of a spine-fusion procedure in which the surgeon also implants one or more cages (neither surgeon nor cage shown in FIGS. 9-10) to hold the graft until the two adjoining vertebrae 1002 are fused (a cage typically stays implanted and is not removed); that is, a surgeon can use one or more rodscrews 100 for spinal fusion with, or without, one or more cages.

In addition, the surgeon can implant a rodscrew 100 such that the distal end 102 engages a bony portion of cancellous or cortical vertebral bone.

Furthermore, a surgeon can countersink the proximal end 106 of the rodscrew 100 such that if the rodscrew is to remain in the patient permanently, bone can grow over the exposed end of the rodscrew to close the opening.

Moreover, although described as being performed on a human, the above-described spine-fusion procedure, or a similar procedure with appropriate modifications, may be performed on any vertebrate in, for example, a veterinary application.

Potential advantages of the above-described spine-fusion procedure using one or more rodscrews 100 include that a surgeon can implant the rodscrew posteriorly (from the back side of the patient)—for many spine surgeries such as spine fusion, the subject is already prone (lying on his/her stomach) so that the subject need not be turned over to implant the rodscrew.

Furthermore, the implantation (particularly posterior implantation) of the rodscrew 100 is minimally invasive and may be safer than implantation or other use of a pedicle screw or a cage (if the rodscrew can replace these devices for the procedure) because forming an entry hole in a non-spinal bone at the spot (e.g., pelvis) from which the surgeon implants the rodscrew is typically safer than operating directly on the anterior spine.

Moreover, the above-described embodiments of a procedure for rodscrew implantation are not designed to replace spinal fusion. Instead, the implanted one or more rodscrews 100 are configured to fix (e.g., secure) the spine in the proper alignment until spinal fusion is complete (solid).

Still referring to FIGS. 1, 9, and 10, alternate embodiments of the described procedure for implanting one or more rodscrews 100 for spine-fusion stabilization, and alternate spine-related procedures utilizing one or more rodscrews, are contemplated. For example, rodscrew implantation could replace more-invasive, and possibly less-successful, types of spine fixation. Furthermore, rodscrew implantation also could augment the posterior spinal fixation with rods, negate the need for pedicle screws, and replace any anterior-fixation devices currently used. Moreover, embodiments described in conjunction with FIGS. 1-9 and 11-42 may be applicable to the spine-fusion-stabilization procedure described in conjunction with FIGS. 9-10.

Scoliosis

Scoliosis is a condition in which the spine is curved in a plane that is not the sagittal (back-to-front) plane in which a normal spine exhibits curvature. For example, a person with scoliosis may have a spine that exhibits curvature in the coronal (side-to-side) plane, which is orthogonal to the sagittal plane; that is, if one looks at a person who suffers from scoliosis from behind, the spine is curved from side-to-side. In most instances of scoliosis, the abnormal curvatures are in the form of helical curves. Furthermore, the curves that characterize scoliosis are typically in the thorax region of the spine.

Scoliosis in children, if not too severe, is typically treated with an external back brace that a child wears for a period of time to attempt to prevent the curve from worsening with growth of the spine. An external back brace is usually used only with a growing child who has a relatively small abnormal spinal curve.

More serious cases of scoliosis may be treated by fusing adjoining vertebrae as described above in conjunction with FIGS. 9-10.

But in an embodiment described below, a surgeon can treat scoliosis in an adult human or a teenager by implanting, in the spine, one or more rodscrews 100, 600, and 700 of FIGS. 1, 5, and 6, respectively. The one or more rodscrews 100, 600, and 700 may be the only treatment device(s) used, or they may be used in conjunction with conventional treatment devices such as posterior compression and distraction rods. For purposes of example, only treatment with one or more rodscrews 100 is described hereinafter, it being understood that treatment with one or more rodscrews 600 and 700 in addition to, or instead of, one or more rodscrews 100 can be similar.

In a conventional procedure for treating scoliosis to correct the abnormal spinal curvature, after freeing up the restricting soft tissues, a surgeon typically puts in a rod with a bumper-jack type of mechanism on it to jack up the concave side of the curve, and puts another rod on the opposite side of the vertebrae to compress the convex side of the curve. These rods are both placed posteriorly.

Advantages of using one or more rodscrews 100 to treat scoliosis include that such treatment is less invasive than extramedullary anterior spinal fixation and is potentially much more mechanically effective than current fixation devices.

Embodiments of the rod-screw implantation procedure described below for treating scoliosis can be similar to the embodiments of the rod-screw implantation procedure for spinal fusion described above in conjunction with FIGS. 9-10, but with the rodscrew-implantation entry location including the pelvis or being other than the pelvis.

Figure 11:
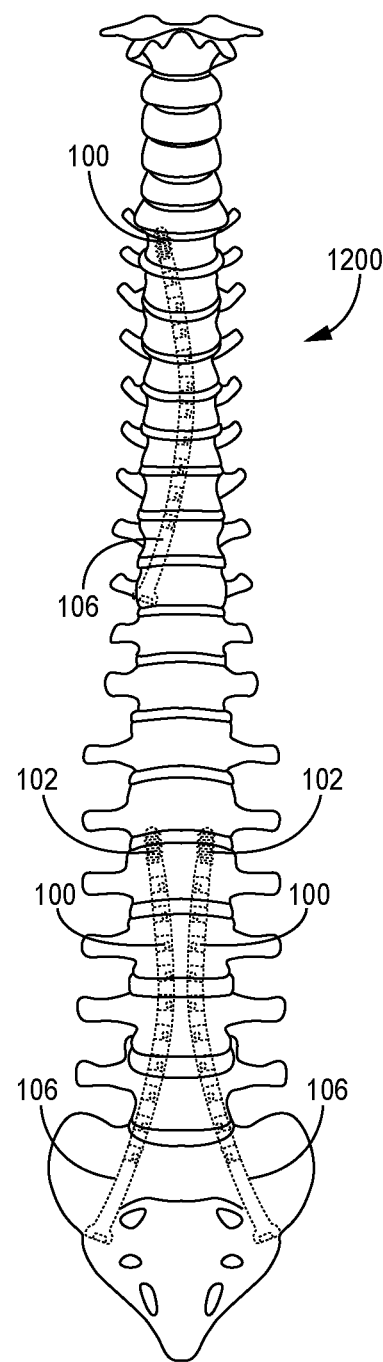
FIGS. 11-12 are views, in the coronal and sagittal planes, respectively, of a human spine in which is implanted one or more of the rodscrews of FIG. 1, 5, or 6, according to an embodiment.
Figure 12:
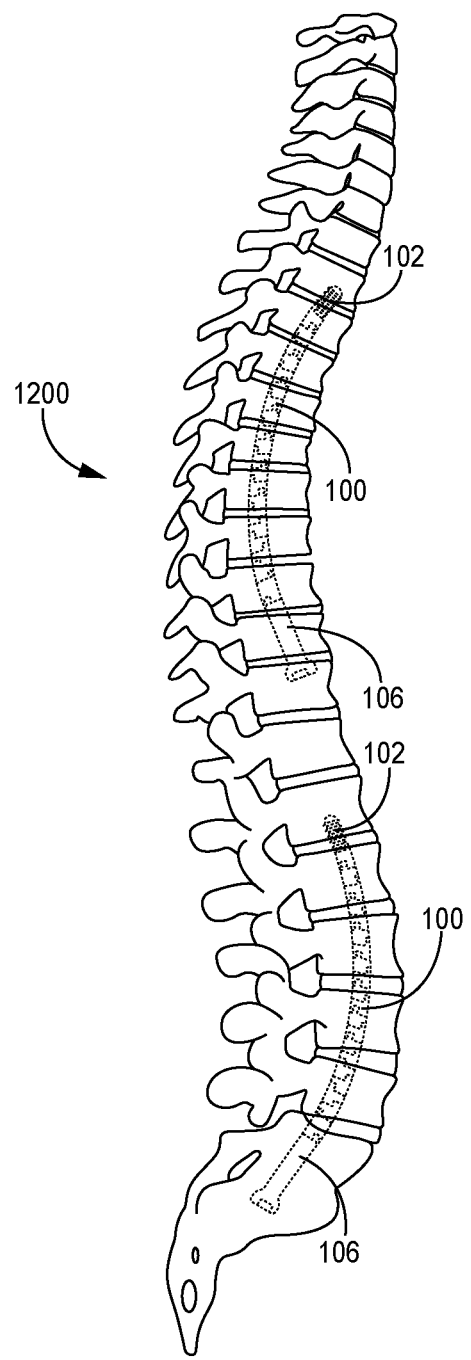

FIGS. 11-12 are views of a human spine 1200 in the coronal and sagittal planes, respectively, in which is implanted one or more rodscrews 100 of FIG. 1.

For example, referring to FIGS. 11-12, instead of "coming in" through the pelvis, a surgeon (not shown in FIGS. 11-12) can form (e.g., drill) an insertion hole in vertebra L1 or in one of the thoracic vertebrae (e.g., T10), and then implant each of one or more rodscrews 100 such that the respective distal end 102 of each rodscrew is disposed in a respective portion of the desired vertebra (e.g., T2).

Furthermore, to avoid the spinal cord and the nerve roots located in the posterior (back side) of the spinal cord, a surgeon can form the rodscrew insertion hole in the anterior (front side), or one of the sides, of the spine. This allows a surgeon flexibility in forming the insertion hole in a location that is most advantageous for a particular subject.

Moreover, each rodscrew 100 can have beveled distal and proximal ends 102 and 106, or can have ends otherwise configured, so that the angle of the insertion or entry hole need not be orthogonal to the surface of the bone in which the hole is formed, but, instead, can be angled from orthogonal. A potential advantage of beveling the distal end 102 of the rodscrew 100 is so that the rodscrew does not "stick out" the side or the front of the vertebral body after it is inserted. Furthermore, an angled insertion hole can reduce the degree of curvature that a rodscrew 100 experiences as it is implanted, and, therefore, can reduce the degree of curvature that the rodscrew attains and holds after it is fully implanted and transitioned to a rigid state.

Still referring to FIGS. 11 and 12, alternate embodiments and advantages of using one or more rodscrews 100 to treat scoliosis are contemplated. For example, embodiments described in conjunction with FIGS. 1-10 and 13-42 may be applicable to the above-described procedure for treating scoliosis with one or more rodscrews 100.

Kyphosis and Kyphoscoliosis

Referring again to FIGS. 9-12, kyphosis is a condition in which a spine is abnormally curved in the sagittal plane (see FIG. 12), and kyphoscoliosis is a combination of kyphosis and scoliosis.

Both kyphosis and kyphoscoliosis in an adult human and in a teenager can be treated with one or more rodscrews 100 in a manner similar to the manner described above for treating scoliosis. And because it is configured to flex simultaneously in more than one plane, a rodscrew 100 is particularly well suited for treating kyphoscoliosis (spine abnormally curved in both the coronal and the sagittal planes).

Fractures of the Proximal Femur

Figure 13:
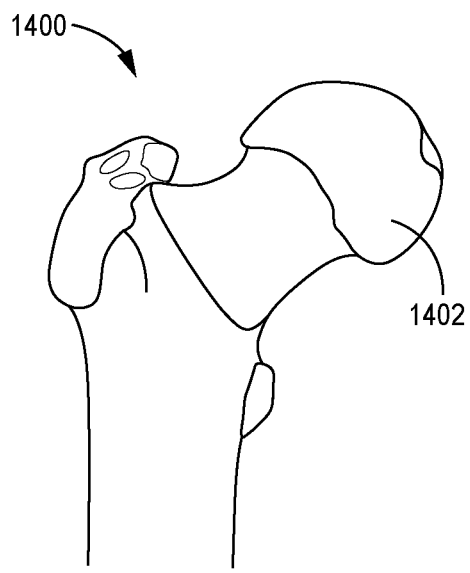
FIG. 13 is a view of a human proximal femur.

FIG. 13 is a view of a human proximal femur 1400.

Figure 14:
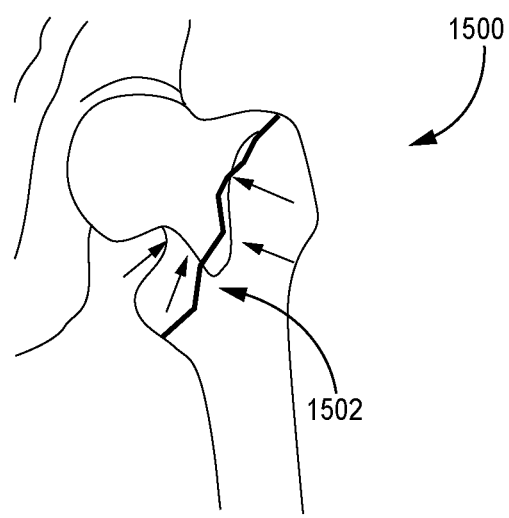
FIG. 14 is a view of a human proximal femur with an intracapsular fracture.

FIG. 14 is a view of a human proximal femur 1500 with an intracapsular fracture 1502.

Figure 15:
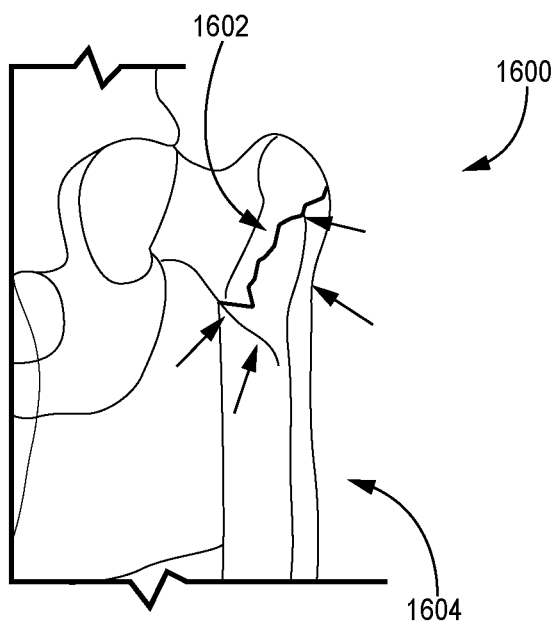
FIG. 15 is a view of a human proximal femur with an intertrochanteric fracture.

FIG. 15 is a view of a human proximal femur 1600 with an intertrochanteric fracture 1602.

Figure 16:
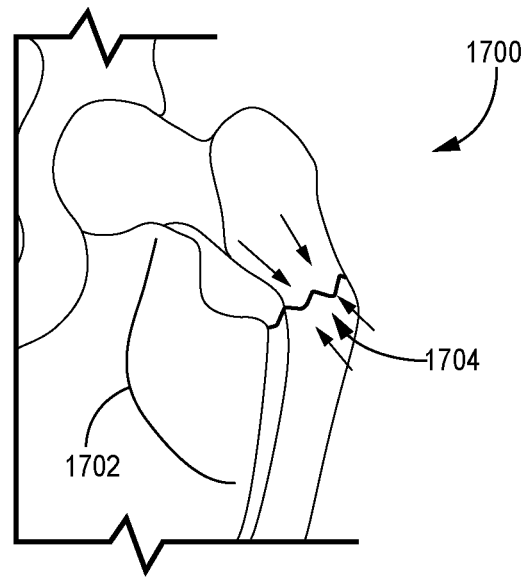
FIG. 16 is a view of a human proximal femur with a subtrochanteric fracture.

FIG. 16 is a view of a human proximal femur 1700 with a subtrochanteric fracture 1702.

Figure 17:
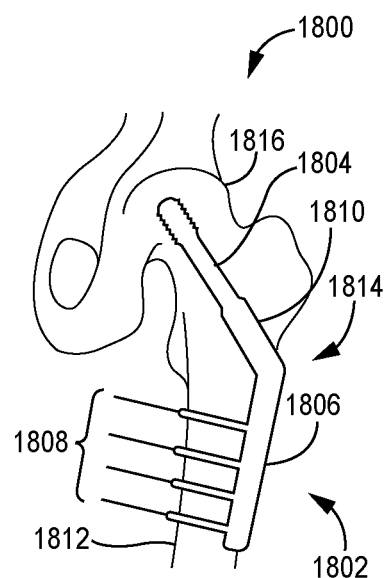
FIG. 17 is a view of a human proximal femur with a fracture fixated with a dynamic hip screw.

FIG. 17 is a view of a human proximal femur 1800 with a fracture fixated with a dynamic hip screw 1802.

Figure 18:
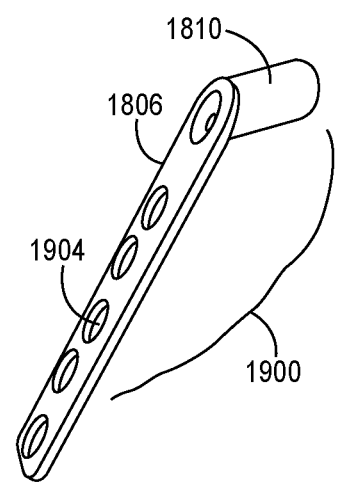
FIGS. 18-19 are views of components of the dynamic hip screw of FIG. 17.
Figure 19:
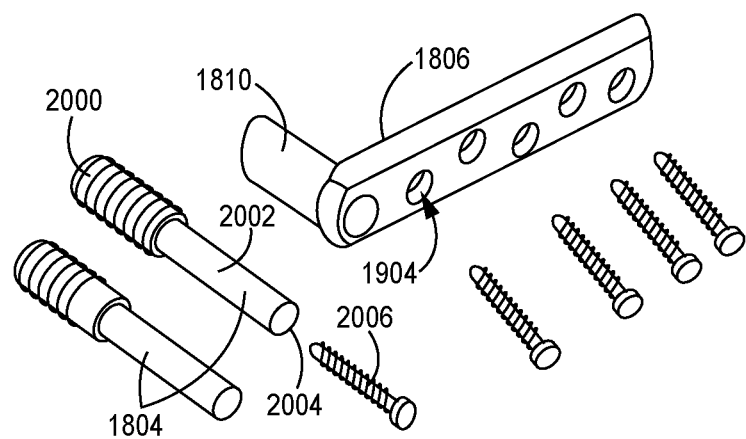

FIGS. 18-19 are views of components of the dynamic hip screw 1802 of FIG. 17.

Figure 20:
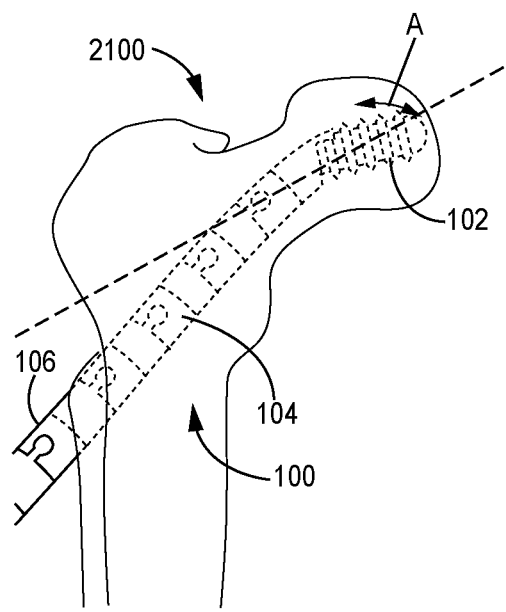
FIGS. 20-21 are coronal and sagittal views, respectively, of a human proximal femur fixated with a rod screw of FIG. 1, 5, or 6, according to an embodiment.
Figure 21:
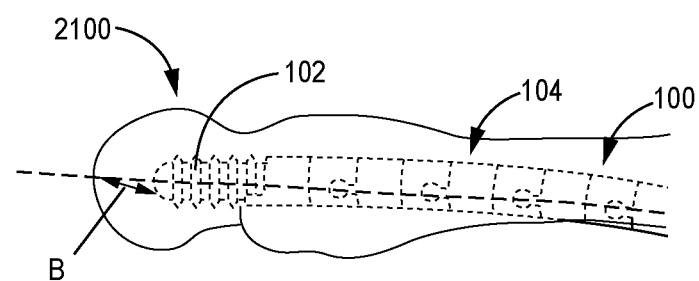

FIGS. 20-21 are coronal and sagittal views, respectively, of a human proximal femur 2100 that can be fixated with one or more rodscrews 100, 600 or 700 of FIG. 1, FIG. 5, or FIG. 6, according to an embodiment. For purposes of example, the proximal femur 2100 is shown, and is described below, as being fixated with one or more rodscrews 100, it being understood that the proximal femur also can be fixated with one or more rodscrews 600 or 700 in addition to, or instead of, one or more rodscrews 100 in a similar manner.

Figure 23:
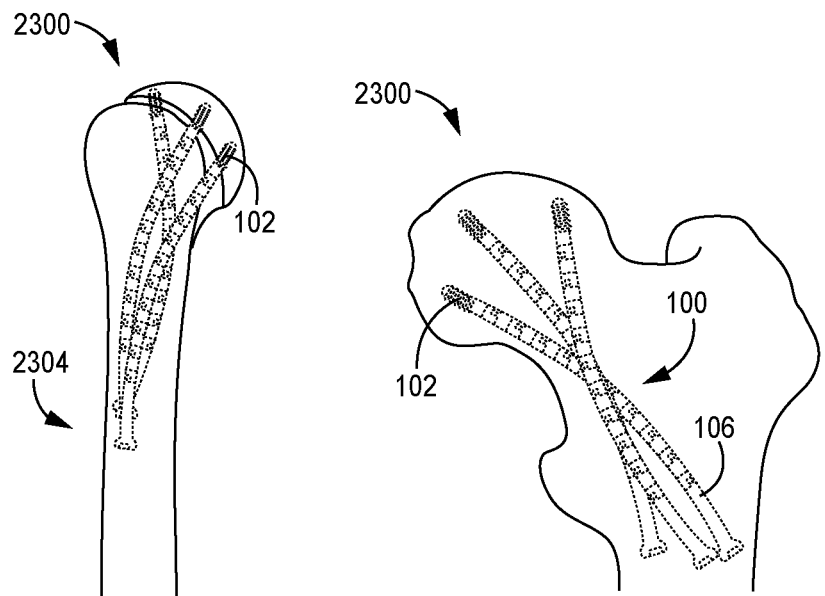
FIGS. 22-24 are views of a human proximal femur and a lower extremity of femur each fixated with multiple rodscrews of FIG. 1, 5, or 6, according to an embodiment.
Figure 22:
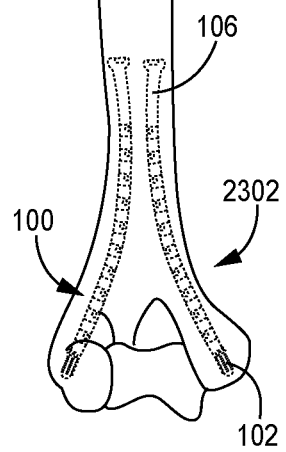
Figure 24:
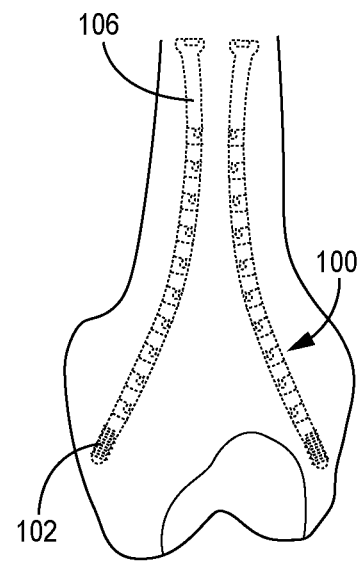

FIGS. 22-24 are views of a human proximal femur 2300 and a lower extremity of femur 2302 that can be fixated with multiple rodscrews 100, 600, or 700 of FIG. 1, FIG. 5, or FIG. 6, according to an embodiment. For purposes of example, the proximal femur 2300 and the lower extremity of femur 2302 are shown, and are described below, as being fixated with one or more rodscrews 100, it being understood that the proximal femur and the lower extremity of femur also can be fixated with one or more rodscrews 600 or 700 in addition to, or instead of, one or more rodscrews 100 in a similar manner.

Referring to FIGS. 13-24, fractures of the proximal femur are also commonly referred to as hip fractures. However, the 'hip' doesn't fracture as it is a joint. Therefore, the term 'hip fracture' is a misnomer as a 'hip fracture' is a fracture of the proximal femur.

As stated above, FIGS. 13-16 are diagrams of proximal femurs 1400, 1500, 1600, and 1700, respectively.

Referring to FIGS. 14-16, three common types of fracture to the proximal femur are an intracapsular fracture 1502 (FIG. 14), an intertrochanteric fracture 1602 (FIG. 15), and a subtrochanteric fracture 1702 (FIG. 16).

Referring to FIG. 15, intertrochanteric fractures, such as the intertrochanteric fracture 1602, account for nearly 50% of fractures around the hip. An intertrochanteric fracture is a specific type of hip fracture. "Intertrochanteric" means "between the trochanters," which are bony protrusions on a femur 1604 (thighbone). Although intertrochanteric fractures typically heal invariably with conservative treatment, a high rate of complications and a high rate of comorbidities makes stable reduction and rigid internal fixation the method of choice. Elderly subjects with poor bone quality due to, e.g., osteoporosis, have a higher rate of fixation failure. Also, if proper precautions are not taken, an intertrochanteric fracture can result in coxa vara deformity, whereby the angle (see angle 1704 of FIG. 16) between the head and the shaft of the femur 1604 is reduced to less than 120°. Therefore, a coxa vara deformity can result in the subject's leg being shortened, and, therefore, in the subject developing a limp.

In a conventional treatment for fractures of the proximal femur in an adult human, a surgeon, such as an orthopedic surgeon, sets the relative positions of the sections of the fractured bone, on either side of the fracture, for proper healing, and inserts screws to hold the sections of the fractured bone in the set position.

For example, as shown in FIG. 17, a dynamic hip screw (DHS) 1802, also called a sliding screw, is a type of orthopaedic implant designed for fixation of certain types of hip fractures (fractures of the proximal femur), and allows controlled dynamic sliding of the femoral-head component along the construct. One common use of the DHS 1802 is internal fixation of intertrochanteric fractures (e.g., the intertrochanteric fracture 1602 of FIG. 15) of the proximal femur, which, as described above, are common in older osteoporotic patients.

There are three components of the dynamic hip screw 1802, including a large straight lag screw 1804 (configured for inserting into the neck of the proximal femur), a side plate 1806, and four cortical screws 1808 (fixated into the proximal femoral shaft). The idea behind the dynamic compression is that the femoral-head component is allowed to move along one plane; since bone responds to dynamic stresses, the native femur may undergo primary healing in which cells join along boundaries, resulting in a robust joint requiring no remodeling.

Rigid fixation with early mobilization of the subject is a primary goal of treatment of an intertrochanteric fracture 1602 (FIG. 15) of the proximal femur. Restoration of mobility of subjects with an intertrochanteric fracture 1602 ultimately depends on the strength of the surgical construct. Today, the DHS 1802 is the most commonly used device for fixating an intertrochanteric fracture of the proximal femur, such as the intertrochanteric fracture 1602 of the proximal femur 1600. The DHS 1802 works on the principle of controlled collapse where dynamic action along the axis of the lag screw 1804 reduces the incidence of screw cut out and reduces the potential for penetration of the lag screw into the hip socket.

The major force acting in a trochanteric fracture (e.g., the intertrochanteric fracture 1602 of FIG. 15 and the subtrochanteric fracture 1702 of FIG. 16) is the joint force through the femoral head (see the femoral head 1402 of FIG. 13). The joint force has two components: 1) a force parallel to the fracture line, which force can cause sliding of the fracture surfaces and inferior displacement and *varus* angulation of the femoral head; and 2) the force perpendicular to the fracture, which force can drive the fracture surfaces together, and, therefore, can cause friction and mechanical interlocking. The aim of fixation of a trochanteric fracture is to use the perpendicular component to drive the surfaces together, and, therefore, to use the perpendicular component to gain stability.

Referring to FIGS. 17-19, two basic principles enhance the ability of the straight lag screw 1804 of the DHS 1802 to slide within a barrel 1810: 1) within the clinical constraints of the fracture geometry, a higher-angle device typically provides less resistance to sliding because the lag-screw longitudinal axis is more closely aligned to the direction of the joint force; and 2) the lag screw being engaged as deeply as possible within the barrel.

FIGS. 18-19 are diagrams of components of the dynamic hip screw (DHS) 1802.

Referring to FIGS. 17-19, the lag screw 1804 is available in different lengths, and the diameter of a distal threaded end 2000 of the lag screw is, for example, 12.5 millimeters (mm) for a lag-screw length of 22 mm. The diameter of a shaft 2002 of the lag screw 1804 is, for example, 8 mm. The inner surface of a proximal end 2004 (located near the side plate 1806) of the lag screw 1804 is threaded for application of, and engagement with, a compression screw 2006. The barrel 1810 for the lag screw 1804 is set at an angle 1900 of approximately 120° to 150°. The slide plate 1806 has oval slots 1904 for fixation to a shaft 1812 of a femur 1814. The compression screw 2006 is screwed into the proximal end 2004 of the lag screw 1804 after the side plate 1806 is fixed to the shaft 1812 of the femur 1814. 150° side plates 1806 may be preferred because the angle of the lag screw 1804 more closely parallels the compressive forces within the femoral neck. However, 135° side plates 1806 may be more easily implanted.

Central placement of the distal threaded end 2000 of the straight lag screw 1804 with deep penetration into a head 1816 of the femur 1814 often yields the best fixation result. Baumgaertner et. al. described the tip apex distance (TAD) to determine the optimal positioning of the lag screw 1804 in the femoral head 1816. The TAD is the sum of the distances from the apex of the femoral head 1816 to the tip of the straight lag screw 1804. A sum of 25 mm or less was found to result in no failures caused by cutting out of the lag screw.

Referring to FIGS. 20-21, a procedure for fixating a fractured portion of a femoral head 2100 with at least one rodscrew 100 of FIG. 1 replacing the lag screw 1804 of the DHS 1802 of FIGS. 17-19 is described, according to an embodiment.

An embodiment of a rodscrew 100, and of a corresponding procedure, for replacing a straight DHS lag screw 1804 (FIGS. 17-19) with the rodscrew 100, includes the following features (the components of the DHS 1802 are omitted from FIGS. 20-21 for clarity):

A straight proximal end 106 along a longitudinal axis (see longitudinal axis 706 of FIG. 6) near the side plate 1806 (FIG. 17).

The straight proximal end 106 includes a shape-lock feature to lock a curvature of the rodscrew 100.

The straight proximal end 106 includes an interface with the side plate 1806 to add compression in a direction perpendicular to the fracture. For example, the compression interface may include a tube (not shown in FIGS. 20-21) with a threaded interior and a rodscrew with a threaded exterior. An alternative embodiment may include an internal mechanism within the rodscrew 100 to add compression after implantation.

The side plate 1806 helps to reduce a potential stress riser at the exterior of the bone where the proximal end 106 of the rodscrew 100 exits the bone. To reduce stress rising near the bone surface, a washer or similar device may be used external to the bone as an alternative.

A threaded distal end 102 for embedding into the femoral head 2100.

A body 104 along the axis of the rodscrew 100, the body being configurable in a flexible state and in a ridge state.

The body 104 along the longitudinal axis of the rodscrew 100 allows for sufficient curvature to position, in an orientation that the implanting surgeon (not shown in FIGS. 20-21) desires, the tip of the distal end 102 in one or more dimensions near the apex of the femoral head 2100. The length, and the maximum radius of curvature, of the body 104 can be configured so that the rodscrew 100 has a suitable strength.

And the above-described configuration of the rodscrew 100 can have one or more of the following advantages:

Using the rodscrew 100 in place of the lag screw 1804 (FIGS. 17-19) can reduce the chances that a surgeon may need to cut the lag screw out of the head of the femur 2100. This is a common failure mode with DHSs 1802 and can result in a subject needing a hip replacement.

Suitable positioning of the distal end 102 of the rodscrew 100 near the apex of the femoral head 2100.

The ability of the rodscrew 100 to achieve a curved shape including one or more arcs. Since the rodscrew 100 may be curved after implantation, the forces which can lead to a straight lag screw 1804 "breaking out" of the head of the femur can be reduced.

The curved shape of the implanted rodscrew 100 can follow the curved force lines of the lateral tensile system, which may lead to improved fracture fixation outcomes.

Because the rodscrew 100 can have a larger diameter than a lag screw 1804, and because the rodscrew can follow a curved pathway, the rodscrew is able to hold larger tensile forces in bone, such as older osteoporotic bone.

Compared to treating a fracture of the proximal femur 2100 conventionally, with a one or more screws, such as a DHS 1802, a rodscrew 100 can provide a better alternative, according to an embodiment. For example, as described below, only one or two rodscrews 100 may be needed in place of three compression screws or a DHS screw 1802, implantation of a rodscrew 100 is less invasive than the implantation of the screws, and a surgeon may be able to remove the rodscrew after the fracture heals more easily than he/she can remove one or more conventional screws.

For example, referring to FIGS. 20-24, a surgeon (not shown in FIGS. 20-24) could implant the rodscrew 100 in a proximal femur 2100, 2300 with or without a side plate 1806 (FIGS. 17-19).

After a surgeon (not shown in FIGS. 20-24) sets the sections of the femur 2304 (FIG. 22) in proper relative positions to promote proper healing of the fracture, he/she makes a small incision in the subject's leg and forms a corresponding hole (not shown in FIGS. 20-24) in the femur in a location that is below alignment with the femoral neck, forms a pathway, and inserts a rodscrew 100 (FIG. 1) into the femur in a manner similar to that described above in conjunction with FIGS. 9-12 for treatment of the spine (e.g., the surgeon uses one or more types of guidewires, reamers, and drills or hammers during the implant procedure as described above in conjunction with FIGS. 9-12). Because the rodscrew 100 is flexible, it can be fully contained (except for perhaps a flanged end portion of the proximal end 106) within the femur 2304 but still can attain a shape that allows for a less invasive implantation (as compared to use of a DHS 1802 and/or a lag screw 1804 of FIGS. 17-19) and may more closely follow the force lines of the lateral tensile system in the proximal femur 2100, 2300. The distal end 102 of the rodscrew 100 can be threaded, or otherwise can be configured, to engage bone in the femoral head (see femoral head 1402 of FIG. 13) by screwing or hammering, and the proximal end 106 of the rodscrew can be threaded, or otherwise can be configured, to engage the femur 2304 at the rodscrew entry hole.

Therefore, not only can a surgeon (not shown in FIGS. 20-24) implant a rodscrew 100 much less invasively than he/she can implant a compression hip screw (DHS) 1802 (FIGS. 17-19), but a rodscrew can provide advantages similar to the advantages that a compression hip screw can provide over regular screws, such similar advantages including an ability to use only one or two rodscrews, and the rodscrew's rigid curved shape preventing unwanted rotations, and other unwanted movements, of the sections of the fractured femur bone relative to one another.

Furthermore, if the fixation device is to be removed after the fracture has healed, then a surgeon (not shown in FIGS. 20-24) can remove the rodscrew 100 with a small incision or no incision (if the face of the proximal end 106 of the rodscrew is left exposed), whereas a surgeon typically must make a relatively large incision to remove a compression hip screw (DHS) 1802.

Referring to FIGS. 13-24, alternate embodiments and advantages of using one or more rodscrews 100 to treat fractures of a femur (e.g., femur 2100 of FIG. 20 and femur 2300 of FIG. 22) are contemplated. For example, embodiments described in conjunction with FIGS. 1-12 and 25-42 may be applicable to the above-described procedures for treating femur fractures with one or more rodscrews 100. Furthermore, as stated above, although described in conjunction with rodscrew(s) 100, the above-described procedures for treating femur fractures can be similar if one or more rodscrews 600 and 700 of FIGS. 6 and 7 are used in place of, or in addition to, the rodscrew(s) 100.

Figure 25:
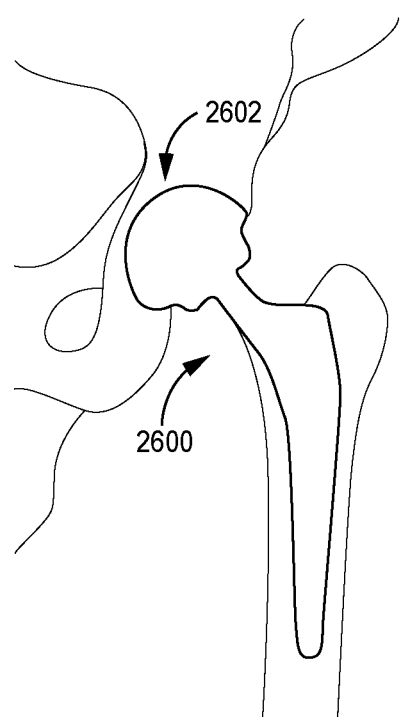
FIG. 25 is a view of hip prosthetic replacing a human hip.

FIG. 25 is a view of hip prosthetic 2600 replacing a human hip.

Figure 26:
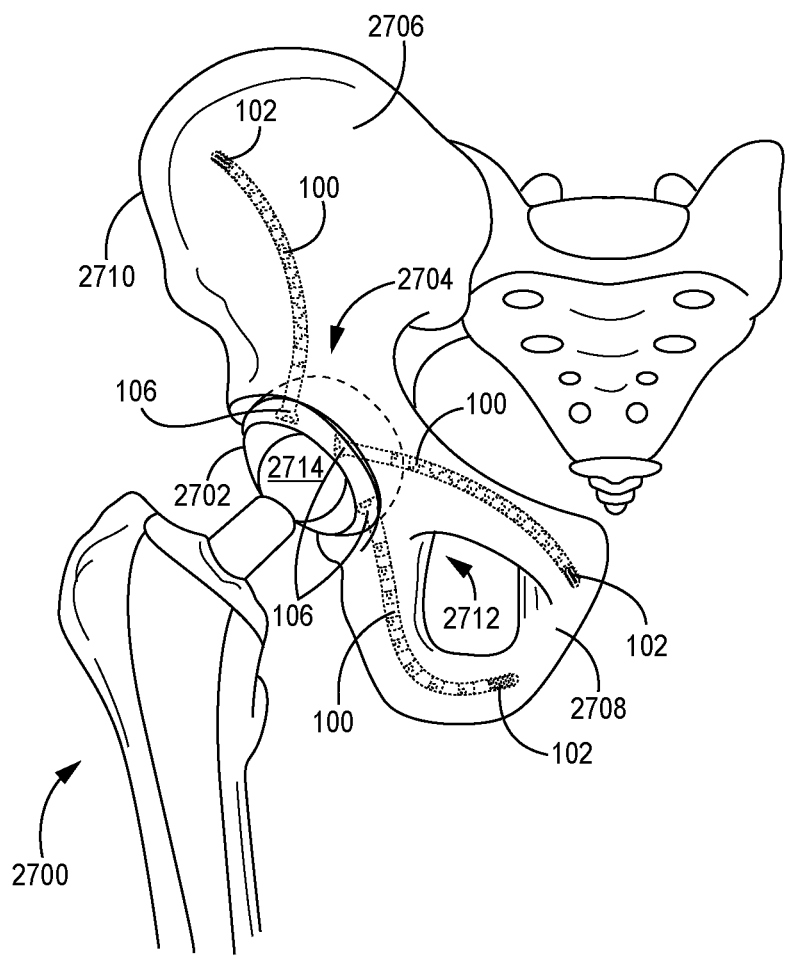
FIG. 26 is a view of a hip prosthetic including an artificial hip socket attached to a human acetabulum (hip socket) with one or more rodscrews of FIG. 1, 5, or 6, according to an embodiment.

FIG. 26 is a view of a hip prosthetic 2700 including an artificial hip socket 2702 attached to a human acetabulum 2704 with one or more rodscrews 100, 600, or 700 of FIGS. 1, 6, and 6, according to an embodiment. For purposes of example, the below-described procedures are described in conjunction with the use of rodscrews 100, it being understood that the procedures can be similar if one or more rodscrews 600 or 700 are used in place of, or in addition to, one or more rodscrews 100.

Figure 27:
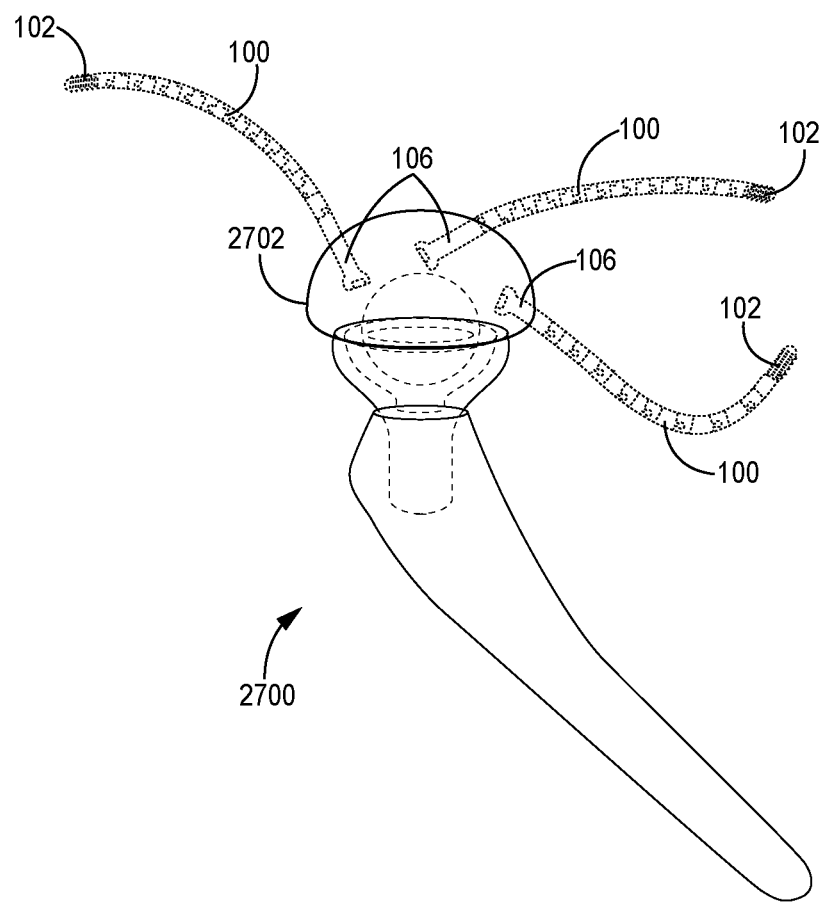
FIG. 27 is a view of the hip prosthetic and the rodscrews of FIG. 26, according to an embodiment.

FIG. 27 is a view of the hip prosthetic 2700 and the rodscrews 100 of FIG. 26, according to an embodiment.

Referring to FIG. 25, another conventional treatment for the above-described types of fractures of the proximal femur in an adult human is a total hip replacement, for example, with a hip prosthetic 2600.

As part of a conventional total hip replacement, an artificial hip socket (i.e., a metal cup or liner, not shown in FIG. 25) is attached to the acetabulum (the natural hip socket) 2602 with one or more screws and cement (neither screws nor cement shown in FIG. 25).

Referring to FIGS. 26-27, one or more rodscrews 100 can be used, instead of, or in addition to, one or more screws or cement, to attach an artificial hip socket 2702 to an acetabulum 2704, according to an embodiment. For example, using one or more rodscrews 100 to attach the artificial hip socket 2702 to the acetabulum 2704 can provide a more stable, and a longer lasting, attachment as compared to conventional screws and cement alone.

Referring to FIGS. 26-27, a surgeon (not shown in FIGS. 26-27) forms one or more holes (e.g., three holes) through, and evenly spaced around, the artificial hip socket 2702 and the acetabulum 2704, and forms through each hole, as described above for the spinal-fusion procedure in conjunction with FIGS. 9-12) (e.g., with one or more types of guidewires, a reamer, and a drill or hammer), a respective curved pathway into the ilium 2706 or into one of the pubic bones 2708. Conventional screws for attaching and securing an artificial hip socket typically can be put into the ilium 2706 via the acetabulum 2704 only a relatively short distance because they are straight. But, at least due to its length and ability to be flexed into a curve and to hold, rigidly, a curved shape, each of one or more rodscrews 100 can be directed up a respective strong column of bone towards the iliac crest 2710, down the posterior column to the ischial spine, or down the superior pubic ramus 2712 (anterior column) to the symphysis. The rodscrews 100 can be made to be longer, wider, and, therefore, more robust than conventional screws.

Next, a surgeon (not shown in FIGS. 26-27) inserts, into each hole, a respective rodscrew 100 in a manner similar to that described above for treatment of the spine (e.g., over a guidewire) in conjunction with FIGS. 9-12. Because each rodscrew 100 is flexible in a flexible configuration, the rodscrew conforms its shape to the shape of the formed path in which it is inserted, which path is typically curved. The distal end 102 of the rodscrew 100 can be threaded, or otherwise configured, to engage bone in the ilium 2706 or pubic arch by screwing or hammering, and the proximal end 106 of the rodscrew can be threaded, or otherwise configured, to engage the artificial socket 2702 and the acetabulum 2704 at the rod-screw entry hole. The proximal end 106 of a rodscrew 100 can be countersunk, and can have a flanged head wider (see FIGS. 2-4) than the body 104 of the rodscrew 100, so that the proximal end holds the artificial socket 2702 in place without extending past the surface of the artificial socket, and, therefore, without potentially interfering with the artificial femoral head 2714 (the face of the proximal end may also be curved with a same radius of curvature as the artificial socket to facilitate smooth rotation of the artificial femoral head within the artificial socket).

Then, a surgeon (not shown in FIGS. 26-27) transitions each rodscrew 100 from its flexible state to its rigid state to lock the rodscrew into its respective shape (typically a curved shape) within its respective path to make the rodscrew rigid and able to support a load.

Because the locked and rigid one or more rodscrews 100 are typically locked into a curved, not straight, shape after implantation, the one or more rodscrews are much less likely to come loose than straight screws. And if, for example, three rodscrews 100 are used and are evenly spaced around the peripheries of the artificial socket 2702 and the acetabulum 2704, then the three rodscrews can form a tripod-like structure, such as that shown in FIGS. 26-27, that securely holds the artificial socket in place against the acetabulum.

Referring to FIGS. 13-27, alternate embodiments of the described techniques for treating fractures of, and the described procedures related to, the proximal femur (e.g., 1400-1700) and the hip are contemplated. For example, embodiments described in conjunction with FIGS. 1-12 and 28-42 may be applicable to the proximal-femur- and hip-related treatments and procedures described in conjunction with FIGS. 13-27.

Fractures of Mandible (Lower Jaw)

FIG. 28 is a side view of a human mandible 2900, and shows types of common mandible fractures, including fractures of the condylar neck 2902, the coronoid process 2904, the ramus 2906, the angle 2908, the body 2910, the canine region 2912, and the symphysis 2914. And each of these types of fractures is often accompanied by a "twin fracture" of the same type on the opposite side of the mandible 2900.

Referring to FIGS. 28-30, the curved shape of the mandible 2900 presents challenges in treating a mandible fracture.

The types of mandible fractures shown in FIG. 28, and other types of mandible fractures, are typically treated by wiring the jaw shut, attaching one or more metal plates (not shown in FIGS. 28-30) external to the mandible 2900 across the fracture to hold the sections on either side of the fracture together to promote healing of the fracture, or both by wiring the jaw shut and using one or more metal plates. In some cases, screws, pins, or nails (not shown in FIGS. 28-30) may be used instead of, or in conjunction with, metal plates. But in just about all cases, the jaw is wired shut to promote healing.

Although wiring a jaw shut is a proven method of promoting healing of a broken mandible 2900, the time for treatment is typically three to six weeks depending on the type and severity of the fracture.

During the time during which a subject's jaw is wired shut, the subject often cannot talk normally.

Furthermore, the subject cannot eat any foods that require chewing or opening of the jaws, and is typically relegated to eating only foods that can be consumed via a straw (the jaw is typically wired such that there is enough room between the upper and lower sets of teeth to accommodate a straw), such as broths, pureed foods, nutrient drinks, shakes, and smoothies.

Moreover, the subject vomiting can give rise to a life-threatening situation by causing suffocation or other health problems as the subject cannot open his/her jaws to expel the vomit.

In addition, the subject cannot yawn normally.

And although using a metal plate is a proven method to treat a fracture of the mandible 2900, use of a metal plate typically requires a surgeon to make a relatively large incision during implanting of the metal plate, and also during removing of the metal plate (if the plate is to be removed).

According to an embodiment, one or more rodscrews 100, 600, or 700 of FIGS. 1 and 5-6, respectively, can be used to promote healing of a broken mandible 2900 without requiring a subject's jaw to be wired shut, and without requiring a large incision during implantation or removal. Although the subject still may be unable to chew foods, the one or more rodscrews 100, 600, or 700 can allow a subject to open his/her mouth to speak, to ingest soft foods, and to vomit. For purposes of example, procedures involving the jaw and mandible 2900 are described in conjunction with the rodscrew 100, it being understood that the procedures may be similar using one or more of the rodscrews 600 or 700 in place of, or in addition to, one or more rodscrews 100.

Referring to FIGS. 29-30, in an embodiment, a surgeon (not shown in FIGS. 29-30) implants each of one or more rodscrews 100 into the mandible 2900 in a manner similar to the manner described above in conjunction with spinal fusion (FIGS. 9-12), such that the each rodscrew spans a one or more respective fractures. Because a rodscrew 100 is flexible in an unlocked configuration, the rodscrew can traverse and occupy a curved path within the mandible 2900. For example, if the fracture is in the canine region 2912 (FIG. 28) of the mandible 2900, then a rodscrew 100 can be inserted on one side of the mandible and curve around the front of the mandible. And if the canine fracture is one of twin canine fractures, then the surgeon can cause a single rodscrew 100 to span both fractures by implanting the rodscrew from one side of the mandible 2900 on a proximal side of a first fracture, and by guiding the rodscrew around the mandible and through the canine region 2912 on the other side of the mandible until a distal end 102 of the rodscrew is on a distal side of the second fracture. Next, the surgeon screws or hammers the rodscrew 100 so that the distal end 102 engages a respective portion of the mandible 2900 on the distal side of the second fracture, and so that the proximal end 106 of the rodscrew engages the opening (not shown in FIGS. 29-30) in the mandible through which the surgeon implanted the rodscrew. Then, the surgeon transitions the rodscrew 100 from a flexible (unlocked) state to a rigid (locked) state to lock the rodscrew into its current curved shape so that the rodscrew holds the spanned sections of the mandible 2900 together to promote healing of the fracture(s).

Because each rodscrew 100 is inside of the mandible 2900 instead of outside like plates, the rodscrew is better at maintaining the sections of the mandible in stable positions relative to one another even while the subject opens and closes his/her mouth.

Therefore, even if a surgeon (not shown in FIGS. 29-30) advises a subject that he/she cannot chew food, the subject can still open his/her mouth to talk, to eat foods that do not require chewing, to vomit, and to yawn.

Furthermore, a surgeon (not shown in FIGS. 29-30) need only make a relatively small incision and hole in the bone of the mandible to implant a rodscrew 100, and to remove the rodscrew after the fracture has healed (if the rodscrew is to be removed).

Still referring to FIGS. 28-30, in an alternate embodiment, because the mandible 2900 is relatively small, a surgeon may ream a path within the intramedullary space of the mandible using a guidewire (neither surgeon nor guidewire shown in FIGS. 28-30), but may insert a rodscrew 100 into the reamed path without using a guidewire.

Inserting a rodscrew 100 into a reamed path without using a guidewire allows use of a rodscrew that has no receptacle for a guidewire; because the guidewire receptacle, or bore, is typically along a central axis of the rodscrew, the lack of a guidewire receptacle allows the rodscrew to be narrower (e.g., to have a smaller diameter, or otherwise to have a smaller width) than it would be if it were to include a guidewire receptacle.

Still referring to FIGS. 28-30, alternate embodiments of a technique for treating a fracture of the mandible 2900 are contemplated. For example, embodiments described in conjunction with FIGS. 1-27 and FIGS. 31-42 may be applicable to a technique for treating a fracture of the mandible 2900, i.e., a lower jaw, of a human or of another animal.

Fractures of the Calcaneus (Heel)

Figure 31:
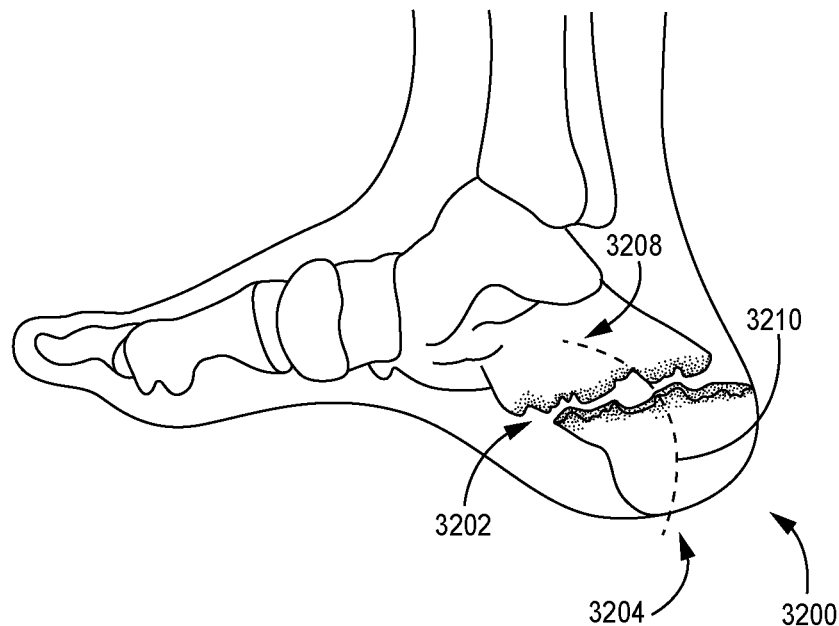
FIG. 31 is a cutaway view of a human foot with a fracture of the calcaneus (heel bone).

FIG. 31 is a side view of a human foot 3200 with a fracture 3202 of the calcaneus (heel bone) 3204. There are at least eight different recognized types of calcaneus fracture, the fracture 3202 being a common type of fracture.

Conventional treatment for Types II-IV (displaced) fractures of the calcaneus 3204 includes using one or more of nails, screws, and plates (not shown in FIGS. 31-33) to stabilize the positions of the sections of the calcaneus bone on either side of each of the one or more fractures relative to one another.

Unfortunately, such conventional treatment often entails making one or more relatively large incisions to expose the fracture(s) 3202 and the sections of the calcaneus bone 3204 on either side of each respective fracture.

Figure 32:
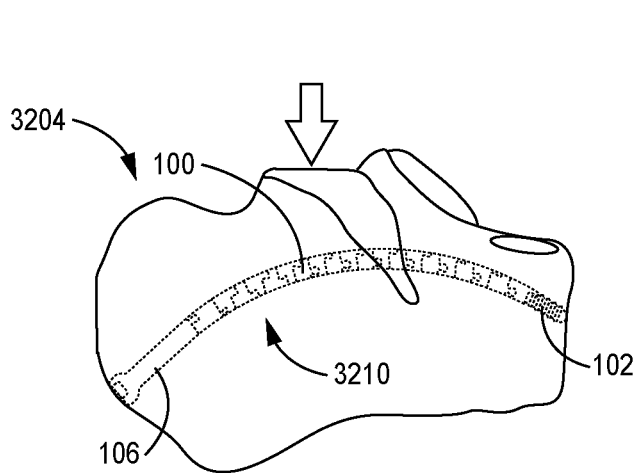
FIGS. 32-33 are respective views of a human calcaneus having implanted therein at least one rodscrew of FIG. 1, 5, or 6 to fixate at least one calcaneus fracture, according to an embodiment.
Figure 33:
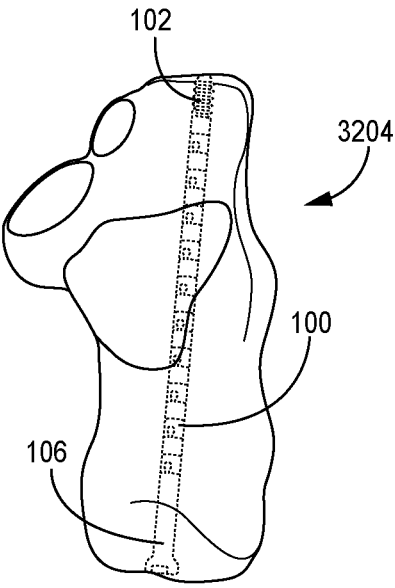

Referring to FIGS. 31-33, in an embodiment, a surgeon (not shown in FIGS. 31-33) can implant one or more rodscrews 100 600, or 700 of FIGS. 1 and 5-6 to treat a fracture of the calcaneus 3204 of an adult. As described above in conjunction with spinal fusion (FIGS. 9-12), a surgeon can implant one or more rodscrews 100, 600, or 700 in a minimally invasive manner because he/she need make only a relatively small incision to expose the portion of the calcaneus 3204 through which he/she will implant the rodscrew. For purposes of example, hereinafter procedures related to the foot 3200 are described with reference only to one or more rodscrews 100, it being understood that the procedures can be similar if a surgeon uses one or rodscrews 600 or 700 in place of, or in addition to, one or more rodscrews 100.

After placing the sections of the fractured calcaneus 3204 in respective positions to promote healing of the fracture(s), a surgeon (not shown in conjunction with FIGS. 31-33) makes an incision, and forms a hole in the calcaneus 3204, at a location 3206, implants each of one or more rodscrews 100 in a manner similar to the manner described above for spinal fusion (FIGS. 9-12) such that a distal end 102 of the rodscrew engages the calcaneus 3204 at a location 3208 and a proximal end 106 of the rodscrew engages the calcaneus at the hole at the location 3206.

Because the rodscrew 100 is flexible while unlocked, a path 3210 between the locations 3204 and 3208 along which the rodscrew lies need not be straight (in the described embodiment the path is curved as shown in FIGS. 32 and 33).

Then, the surgeon (not shown in FIGS. 31-33) transitions each rodscrew 100 to a rigid state, such that the rodscrew rigidly retains its curved shape along the respective path 3210, and, therefore, such that the rodscrew can sustain a load while retaining its curved shape.

After the fracture is healed, a surgeon (not shown in FIGS. 31-33) can remove each rodscrew 100 in a manner similar to the manner described above in conjunction with spinal fusion (FIGS. 9-12).

Still referring to FIGS. 31-33, alternate embodiments of a technique for treating a calcaneus fracture are contemplated. For example, embodiments described in conjunction with FIGS. 1-30 and 34-42 may be applicable to a technique for treating a fracture 3202 of the calcaneus 3204.

Fractures of Bones in Adolescents

Figure 34:
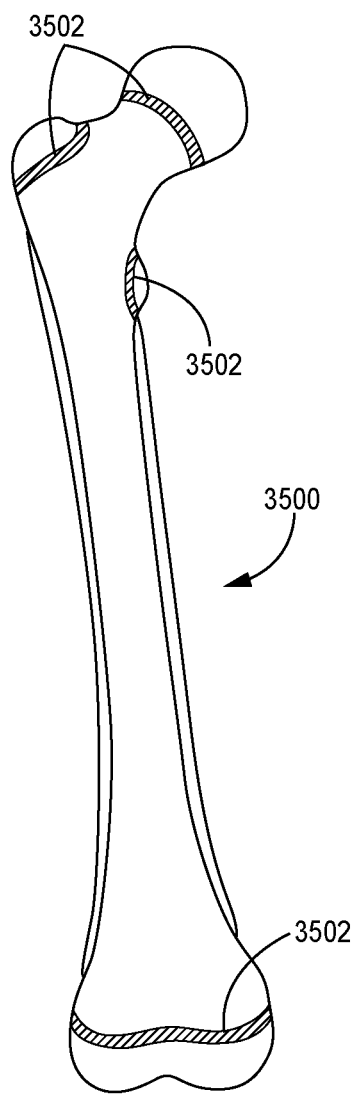
FIG. 34 is a view of a human adolescent femur and growth plates of the femur.

FIG. 34 is a view of a human adolescent femur 3500 and growth plates 3502 of the femur.

Figure 35:
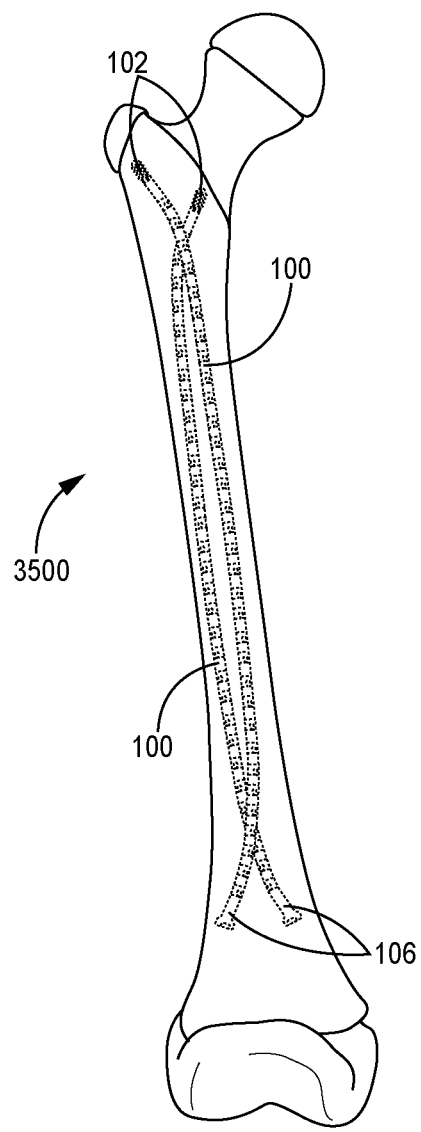
FIG. 35 is a view of the human adolescent femur of FIG. 36 with one or more rodscrews of FIG. 1, 5, or 6 implanted to fixate at least one fracture of the femur without crossing, or otherwise interfering with, growth plates, according to an embodiment.

FIG. 35 is a view of the human adolescent femur 3500 of FIG. 34 with one or more rodscrews 100, 600, or 700 of FIGS. 1 and 5-6 implanted to fixate at least one fracture of the femur while avoiding growth plates 3502, according to an embodiment. For purposes of example, procedures for avoiding growth plates while fixating a bone are described in conjunction with only one or more rodscrews 100, it being understood that the procedures may be similar if performed with one or more rodscrews 600 or 700 in place of, or in addition to, one or more rodscrews 100.

Referring to FIGS. 34-35, the above-described and below-described treatments for fractures of various bones, for treating joint separations, for holding implant pieces in place, and for related purposes, can be adapted (if needed) as described below for an adolescent subject who is still growing. That is, the above-described and below-described treatments and procedures can be adapted (if needed), as described below, so as not to interfere with, or otherwise negatively affect, the growth of the treated region, or another region, of the adolescent subject's body.

A growth plate is a region of a bone where growth of the bone occurs in an adolescent whose body has yet to stop growing, i.e., an adolescent whose body is still growing.

For example, FIG. 34 shows the femur 3500 of an adolescent subject and growth plates 3502 of the femur.

Other bones in the body of an adolescent, including, but not limited to, the humerus, radius, ulna, scapula, clavicle, mandible, rib, calcaneus, pelvis, and vertebra (none of these other bones shown in FIGS. 34-35), each have one or more similar growth plates.

A screw, pin, or nail cannot be implanted through a growth plate, and a metal plate cannot span a growth plate, to treat a fracture of an adolescent's bone because this can stunt, or otherwise can affect, negatively, growth of the bone.

A conventional technique to stabilize a fracture in a long bone (e.g., the femur 3500, the humerus) of an adolescent subject is to implant multiple flexible nails, called Nancy Nails (not shown in FIGS. 34-35), which avoid the growth plates.

Adolescent subjects' femurs (see, e.g., the femur 3500) are often treated with Nancy Nails (not shown in FIGS. 34-35). Because the Nancy Nails are flexible at all times, and cannot be made rigid after implant, a surgeon (not shown in FIGS. 34-35) typically implants at least two Nancey Nails evenly spaced around the long bone to prevent rotation of the section of the bone on one side of the fracture relative to the section of the bone on the other side of the fracture.

In addition to the cost and the time of implanting multiple Nancy Nails (not shown in FIGS. 34-35), implanting a Nancy Nail at one location can be more difficult than implanting a Nancy Nail at another location. That is, implanting multiple Nancy Nails may incur even more cost and time because a surgeon (not shown in FIGS. 34-35) cannot implant just one Nancy Nail at the easiest implant location.

Furthermore, after the fracture is healed, a surgeon must remove multiple Nancy Nails, if the Nancy Nails are to be removed (neither surgeon nor Nancy Nails shown in FIGS. 34-35).

In contrast, referring to FIG. 35, in an embodiment, a surgeon (not shown in FIGS. 34-35) can implant one or more rodscrews 100 to treat a fracture (not shown in FIG. 35) of a bone of an adolescent subject while avoiding the one or more growth plates (e.g., the growth plates 3502 of FIG. 34) of the bone (e.g., the femur 3500 of FIG. 34).

Because the rodscrew 100 can be made rigid in a curved shape after implant, a single rodscrew, locked in a curved shape, can prevent rotation of a bone section on one side of a fracture relative to a bone section on the other side of the fracture.

Implanting only a single rodscrew 100 can reduce at least the time required for the surgery, and can allow the surgeon (not shown in FIGS. 34-35) to implant the single rodscrew from the most favorable implant location for a particular subject.

Furthermore, implanting only a single rodscrew 100 can decrease the complexity of, and the time required for, removing the rodscrew after the bone has healed.

Referring to FIGS. 34-35, in an embodiment, a surgeon (not shown in FIGS. 34-35) implants, in a long bone (e.g., a femur 3500) of an adolescent subject, a rodscrew 100 in a manner (e.g., making a relatively small incision, forming a hole, using one or more types of guidewires, a reamer, and a drill or hammer) similar to the manner described above in conjunction with FIGS. 9-12 for spinal fusion. For example, the surgeon forms a hole in a side of the femur 3500, away from the growth plates 3502, and inserts the rodscrew along a curved path such that no portion of the rodscrew intersects, or otherwise is too close to, a growth plate. One or both of the proximal and distal ends 106 and 102, respectively, of the rodscrew 100 can be beveled or otherwise angled so that the distal end can engage the bone at an angle, and the hole formed in the bone can have a central axis that is other than orthogonal to the surface of the bone.

In one or more similar embodiments, a surgeon (not shown in FIGS. 34-35) can implant one or more rodscrews 100 in a bone of an adolescent subject other than a long bone according to a technique that allows each of the one or more rodscrews to avoid the growth plate(s) of the bone.

Referring to FIGS. 34-35, alternate embodiments of a technique for treating fractures of, and procedures related to, adolescent bones are contemplated. For example, a surgeon may implant more than one rodscrew 100 into a long bone to fixate one or more fractures of the long bone. Furthermore, embodiments described in conjunction with FIGS. 1-33 and 36-42 may be applicable to a technique for treating fractures of, and procedures related to, bones of adolescent subjects who are still growing.

Separation of the Shoulder

Figure 36:
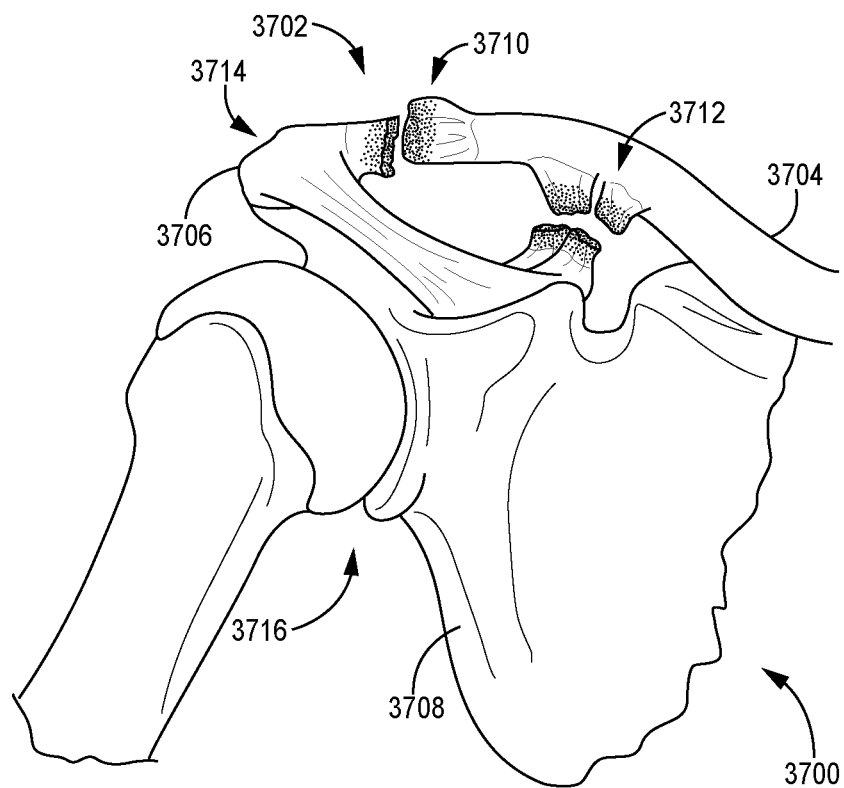
FIG. 36 is a diagram of a human shoulder including an acromioclavicular (AC) joint with a grade III separation that can be fixated with one or more rodscrews of FIG. 1, 5, or 6, according to an embodiment.

FIG. 36 is a diagram of a human shoulder 3700 including an acromioclavicular (AC) joint 3702 with a grade III separation that can be fixated with one or more rodscrews 100, 600, or 700 of FIGS. 1 and 5-6, according to an embodiment. For purposes of example, procedures for treating the shoulder are described using only one or more rodscrews 100, it being understood that the procedures may be similar if one or more of the rodscrews 600 or 700 are used in place of, or in addition to, one or more rodscrews 100.

Referring to FIG. 36, shoulder separation is a separation of the acromioclavicular joint 3702, commonly referred to as the AC joint, which is the joint between the clavicle (commonly called the "collar bone") 3704 and the acromion 3706, which is the uppermost portion of the scapula 3708 (commonly called the "shoulder blade").

The severity of a separation of the AC joint 3702 ranges from Grade I, which is the least severe and in which no tear is present in the AC ligament 3710 or in the coracoclavicular ligament 3712, to Grade III, which is the most severe and which may include a full tear in one or both of the AC and coracoclavicular ligaments (full tear in both ligaments shown in FIG. 36).

A conventional technique for treating a Grade III separation of the AC joint 3702 is to suture the ligaments 3710 and 3712 and to use one or more straight screws (not shown in FIG. 36) to hold the AC joint together while the torn ligaments (and other tissues, such as cartilage) heal.

Because the acromion 3706 and clavicle 3704 are curved, a surgeon (not shown in FIG. 36) typically uses a number of straight screws inserted at different angles and locations to treat a Grade III separation of the AC joint 3702.

But using straight screws may leave significant permanent scarring, and even temporary or permanent nerve damage (e.g., numb spots in the upper chest).

In contrast, in an embodiment, a surgeon may implant a single rodscrew 100 (neither rodscrew nor surgeon shown in FIG. 36) to treat a Grade III separation of the AC joint 3702. Such a procedure may cause significantly less scarring as compared to using multiple straight screws, and may cause little or no nerve damage.

Referring to FIGS. 1 and 36, in an embodiment, after a surgeon (not shown in FIGS. 1 and 36) positions the acromion 3706 and clavicle 3704 for proper healing, he/she forms a hole in a proximal end 3714 of the acromion closest to the glenoid 3716 (shoulder socket), forms a path (not shown in FIGS. 1 and 36) through the intramedullary cavity of the acromion to a distal end of the acromion facing the clavicle, forms a hole through the distal end of the acromion, and then forms a corresponding hole through a proximal end of the clavicle facing the distal end of the acromion, using guidewires, a reamer, and a drill or hammer in a manner similar to that described above in conjunction with FIGS. 9-12 for spinal fusion. Because the acromion 3706 and clavicle 3704 are curved, the formed path is likely to include one or more bends or curves.

Then, the surgeon (not shown in FIGS. 1 and 36) inserts a rodscrew 100 into the path (not shown in FIGS. 1 and 36), engages a distal end 102 of the rodscrew with a portion of the clavicle 3704, and engages a proximal end 106 of the rodscrew with the entry hole in the proximal end 3714 of the acromion 3706.

Next, the surgeon (not shown in FIGS. 1 and 36) transitions the rodscrew 100 to a rigid state to lock the rodscrew in its current, most likely curved, shape to hold the acromion 3706 and the clavicle 3704 in proper position and alignment, relative to one another, for healing.

Then, the surgeon (not shown in FIGS. 1 and 36) repairs the ligaments 3710 and 3710, cartilage, and other tissues if he/she hasn't already done so; for example, the surgeon may repair the ligaments and cartilage (e.g., by suturing) before implanting the rodscrew.

After the AC joint 3702 has healed, a surgeon (not shown in FIGS. 1 and 36) can remove the rodscrew 100 from the hole through the proximal end 3714 of the acromion 3706. Removal of the rodscrew 100 may increase the range of motion about the AC joint 3702, and may increase the comfort of the subject over the long term.

Fractures of the Clavicle

Still referring to FIGS. 1 and 36, a surgeon (not shown in FIGS. 1 and 36) may use a rodscrew 100 to treat a fracture of the clavicle 3704 (i.e., collar bone) in a manner similar to that described above for treating separation of the shoulder, except that the surgeon forms the implant hole in the clavicle, and the rodscrew is fully contained within the clavicle after implantation. That is, for a fracture of the clavicle 3704 with no accompanying shoulder separation, the rodscrew 100 may not extend into the AC joint 3702 or into the acromion 3706.

If the clavicle 3704 is fractured and there is a separation of the shoulder 3700, then a surgeon (not shown in FIGS. 1 and 36) may use a single rodscrew 100 to treat both the shoulder separation and the fracture by implanting the rodscrew in the manner described above for treating a shoulder separation such that the rodscrew also spans the fracture of the clavicle.

Alternatively, a surgeon (not shown in FIGS. 1 and 36) may implant multiple rodscrews 100 into the clavicle 3704.

Still referring to FIG. 1 and FIG. 36, alternate embodiments of techniques for treating a separation of an AC joint 3702 and for treating (e.g., fixating) a fractured clavicle 3704 are contemplated. For example, a rodscrew 100 may extend any suitable distance into the clavicle 3704 from the acromion 3706. Furthermore, instead of starting the formation of the path at the acromion 3706 and ending the path in the clavicle 3704, a surgeon may start the formation of the path at the clavicle (make a hole in the side of the clavicle) and end in the acromion. Moreover, multiple rodscrews 100 may be used. In addition, embodiments described in conjunction with FIGS. 1-35 and 37-43 may be applicable to a technique for treating a separation of an AC joint 3702 or a technique for treating a fractured clavicle 3704.

Fractures of the Proximal Humerus

Figure 37:
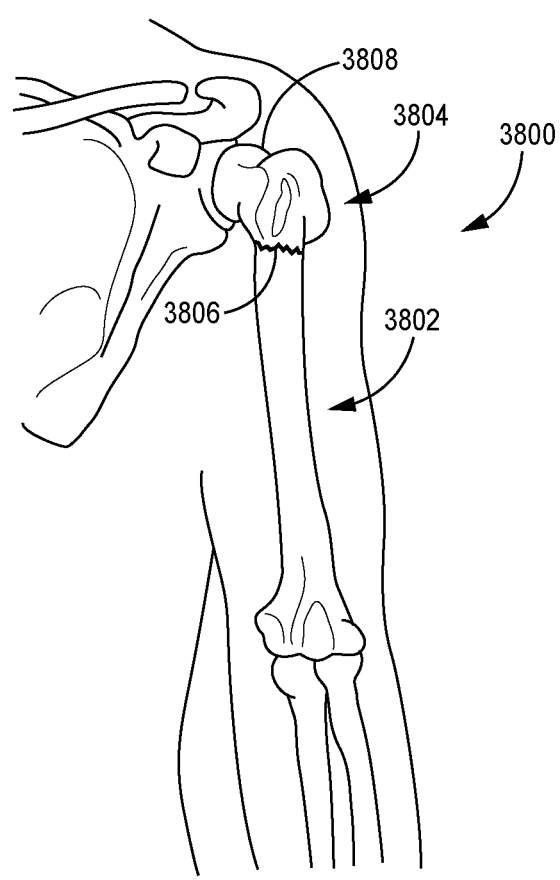
FIG. 37 is a diagram of a human arm with a proximal-humerus fracture that can be fixated with one or more rodscrews of FIG. 1, 5, or 6, according to an embodiment.

FIG. 37 is a diagram of a human arm 3800 with a humerus 3802 having a proximal humerus 3804 with a proximal-humerus fracture 3806, which can be fixated with one or more rodscrews 100, 600, or 700 of FIGS. 1 and 6-7, according to an embodiment.

Figure 38:
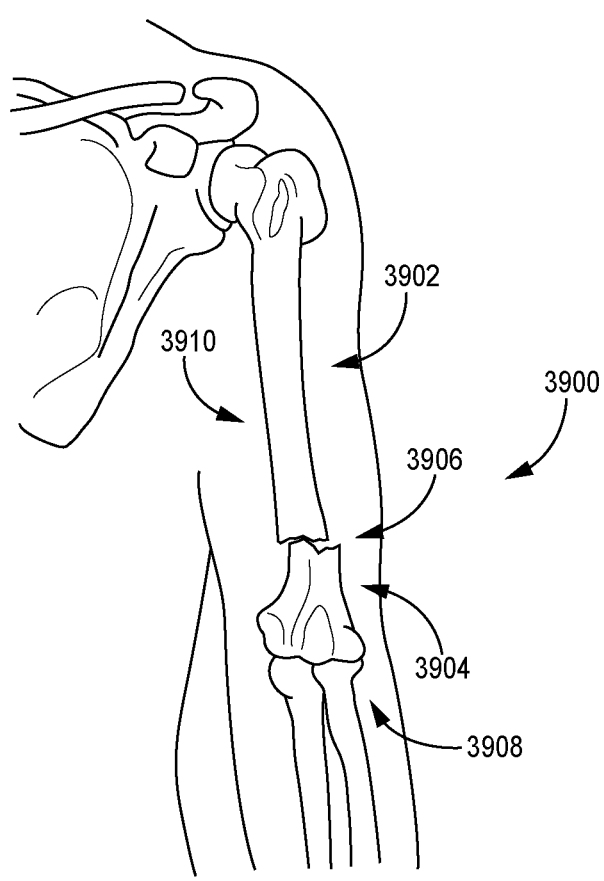
FIG. 38 is a diagram of a human arm with a distal-humerus fracture that can be fixated with one or more rodscrews of FIG. 1, 5, or 6, according to an embodiment.

FIG. 38 is a diagram of a human arm 3900 with a humerus 3902 having a distal humerus 3904 with a distal-humerus fracture 3906, which can be fixated with one or more rodscrews 100, 600, or 700 of FIGS. 1 and 6-7, according to an embodiment.

Figure 41:
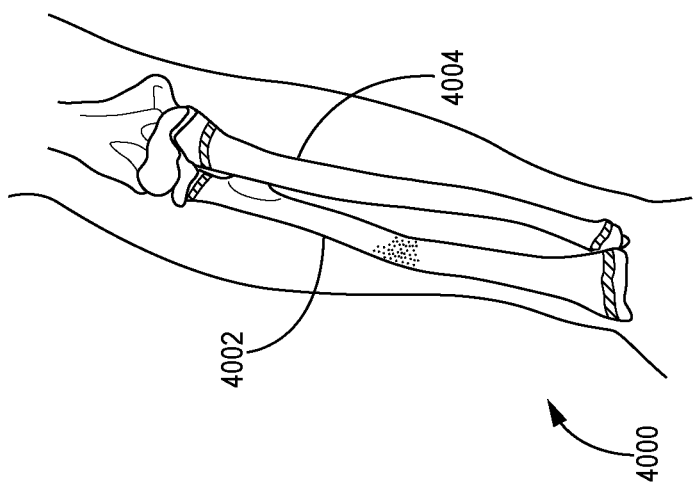
FIGS. 39-41 are respective views of a human arm with respective fractures of the radius and ulna that can be fixated with one or more rodscrews of FIG. 1, 5, or 6, according to an embodiment.
Figure 40:
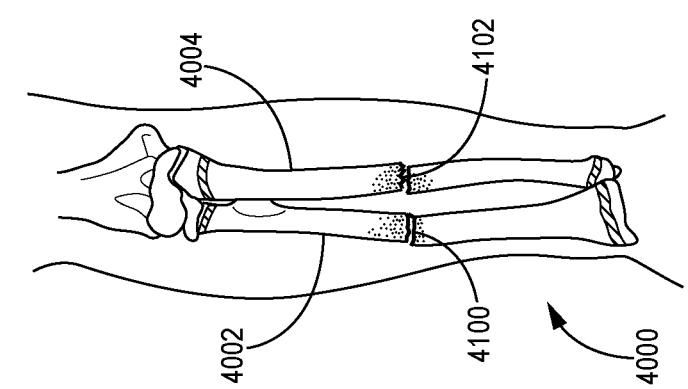
Figure 39:
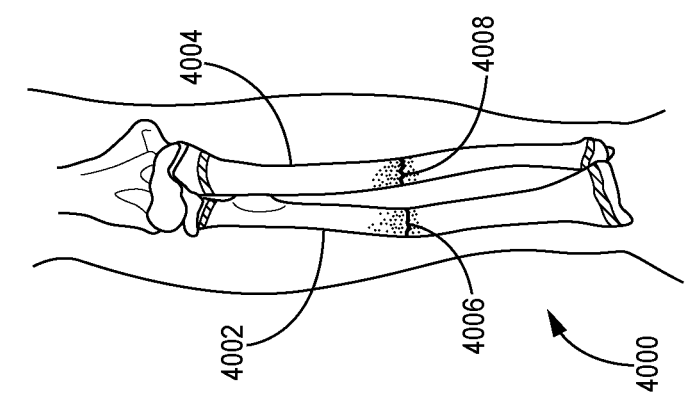

FIGS. 39-41 are respective views of a human arm 4000 with a radius 4002 and an ulna 4004 having respective fractures 4006 and 4008, and 4100 and 4102, which fractures can be fixated with one or more rodscrews 100, 600, or 700 of FIGS. 1 and 6-7, according to an embodiment.

Referring to FIGS. 37-41, for purposes of example, the described procedures for treating an arm fracture are described as using one or more rodscrews 100 of FIG. 1, it being understood that the procedures may be similar if one or more rodscrews 600 or 700 are used with, or instead of, the one or more rodscrews 100.

Referring to FIGS. 1 and 37, a fracture 3806 of the proximal humerus 3804 (the end of the bone of the upper arm that engages the shoulder socket) of an adult human can be treated with one or more rodscrews 100 in a manner similar to the manner described above in conjunction with FIGS. 13-24 for treating a fracture of the proximal femur with one or more rodscrews.

Furthermore, advantages of using a rodscrew 100 to treat a fracture of or near the proximal humerus 3804, as compared to using conventional techniques such as screws and plates, include that a surgeon (not shown in FIGS. 1 and 37) can implant and remove a rodscrew in a less invasive manner than he/she can implant and remove screws or plates.

In an embodiment, after properly positioning the sections of the humerus 3802 on either side of the fracture 3806, a surgeon (not shown in FIGS. 1 and 37) makes a small incision in the arm 3800 and a hole (not shown in FIGS. 1 and 37) along the side of the humerus, and inserts a rodscrew 100 through the hole, and through the intramedullary space of the humerus so that the rodscrew spans the fracture 3806 and the distal end 102 of the rodscrew is located in or near the ball 3808 of the humerus. Because the rodscrew 100 is flexible while unlocked, the rodscrew can follow a curved path (not shown in FIG. 37) from the hole to the ball 3803 of the humerus 3802.

Then, the surgeon (not shown in FIGS. 1 and 37) engages the distal end 102 of the rodscrew 100 in the bone of the humerus 3802 by screwing or hammering, engages the proximal end 106 of the rodscrew into the insertion hole in a similar manner, and transitions the rodscrew to a rigid state to lock the rodscrew into its current shape, which is typically curved. One or both of the proximal and distal ends 106 and 102 of the rodscrew 100 may be beveled/angled. For example, a beveled/angled distal end 102 allows the distal end to engage the bone at an angle, and a beveled/angled proximal end 106 allows the implantation hole through the humerus 3802 to be angled (e.g., to be other than normal to the bone surface).

After the humerus 3802 has healed, a surgeon (not shown in FIGS. 1 and 37) may remove the rodscrew 100 by making a small incision, transitioning the rodscrew back to its flexible state (e.g., unlocking the rodscrew), and removing the rodscrew by reverse hammering or unscrewing.

Still referring to FIG. 37, alternate embodiments of a technique for treating fractures of, and procedures related to, the proximal humerus 3804 are contemplated. For example, embodiments described in conjunction with FIGS. 1-36 and 38-42 may be applicable to a procedure for treating fractures of, and techniques related to, the proximal humerus 3804.

Fracture of Distal Humerus

FIG. 38 is an illustration of a fracture 3906 of a distal humerus 3904 in a human.

Referring to FIGS. 1 and 38, a fracture 3906 of the distal humerus 3904 (the end of the bone of the upper arm that forms part of the elbow) in an adult can be treated with one or more rodscrews 100 by inserting the one or more rodscrews through the end of the humerus 3902, at the elbow 3908, according to an embodiment.

Furthermore, advantages of using a rodscrew 100 to treat a fracture of or near the distal humerus 3904 as compared to using conventional techniques such as screws and plates include that a surgeon (not shown in FIGS. 1-38) can implant and remove the rodscrew in a less invasive manner than he/she can implant and remove screws or plates.

Referring to FIGS. 1 and 38, in an embodiment, after properly positioning the sections of the humerus 3902 on either side of the fracture 3906 for proper healing of the fracture, a surgeon makes a small incision in the elbow 3908, forms a hole in the end the humerus, and inserts a rodscrew 100 through the hole, and through the intramedullary space of the humerus so that the rodscrew spans the fracture and the distal end 102 of the rodscrew is located in or near a midsection 3910 of the humerus (neither surgeon nor entry hole shown in FIGS. 1 and 38). The surgeon can perform these aforementioned steps in a manner similar to that described above for spinal fusion in conjunction with FIGS. 9-12. Because the rodscrew 100 is flexible, it can follow a curved path (not shown in FIGS. 1 and 38) from the hole to the midsection 3910 of the humerus 3902.

Then, the surgeon (not shown in FIGS. 1 and 38) engages the distal end 102 of the rodscrew 100 in the bone of the midsection 3910 of the humerus 3902 by screwing or hammering, engages the proximal end 106 of the rodscrew in the insertion hole in a similar manner, and transitions the rodscrew from a flexible state to a rigid state to lock the rodscrew into its current shape, which, as stated above, may include one or more curves. One or both of the proximal and distal ends 106 and 102 of the rodscrew 100 may be beveled/angled. For example, a beveled/angled distal end 102 allows the distal end to engage the humerus bone 3902 at an angle, and a beveled/angled proximal end 106 allows the hole through the elbow 3908 end of the humerus to be angled.

After the distal humerus 904 has healed, a surgeon (not shown in FIGS. 1 and 38) may remove the rodscrew 100 by making a small incision, transitioning the rodscrew back to its flexible state (e.g., by unlocking the rodscrew), and removing the rodscrew by reverse hammering or unscrewing.

Alternate embodiments of a technique for treating fractures of, and procedures related to, the distal humerus 3904 are contemplated. For example, embodiments described in conjunction with FIGS. 1-37 and 39-43 may be applicable to a procedure for treating fractures of, and techniques related to, the distal humerus 3904.

Fractures of the Radius and the Ulna

FIGS. 39-41 are respective illustrations of types of fractures of the radius 4002 and the ulna 4004, which are both curved bones of the lower arm between the elbow and the wrist.

A fracture of the radius 4002 or ulna 4004 of an adult can be treated with one or more rodscrews 100 (FIG. 1) by inserting each of the one or more rodscrews into a respective hole formed in a suitable location of the fractured bone. For example, in an adult, the hole can be located at an end, such as the elbow end, of the fractured bone.

Furthermore, advantages of using a rodscrew 100 (FIG. 1) to treat a fracture of the radius 4002 or ulna 4004, as compared to using conventional techniques such as using screws and plates, include that a surgeon (not shown in FIGS. 39-41) can implant and remove a rodscrew in a less invasive manner than he/she can implant and remove screws or plates.

Referring to FIGS. 1 and 39-41, in an embodiment, after properly positioning the sections of the fractured one of the radius 4002 and ulna 4004 on either side of the fracture (e.g., radial fracture 4006 or ulnal fracture 4008), a surgeon (not shown in FIGS. 1 and 39-41) makes a small incision at the location for the hole, forms the hole (not shown in FIGS. 1 and 39-41) in the bone, and inserts a rodscrew 100 through the hole, and through the intramedullary space of the bone so that the rodscrew spans the fracture. The surgeon may perform these steps in a manner similar to that described above for spinal fusion in conjunction with FIGS. 9-12. Because the rodscrew 100 is flexible while unlocked, it can follow the curvature of the fractured bone.

Then, the surgeon (not shown in FIGS. 1 and 39-41) engages the distal end 102 of the rodscrew 100 in the bone by screwing or hammering, engages the proximal end 106 of the rodscrew into the insertion hole (not shown in FIGS. 1 and 39-41) in a similar manner, and transitions the rodscrew to a rigid state to lock the rodscrew into its current shape, which may be a curved shape. One or both of the proximal and distal ends 106 and 102 of the rodscrew 100 may be beveled/angled. For example, a beveled/angled distal end 102 allows the distal end to engage the bone at an angle, and a beveled/angled proximal end 106 allows the hole through the elbow end of the radius 4002 or ulna 4004 to be angled relative to the surface of the bone near the hole.

After the bone (i.e., the radius 4002 or the ulna 4004) has healed, a surgeon (not shown in FIGS. 1 and 39-41) may remove the rodscrew 100 by making a small incision, transitioning the rodscrew back to its flexible state, and removing the rodscrew by reverse hammering or unscrewing.

Alternate embodiments of a technique for treating fractures of, and procedures related to, the radius 4002 and ulna 4004 are contemplated. For example, embodiments described in conjunction with FIGS. 1-38 and 42 may be applicable to a procedure for treating fractures of, and techniques related to, the radius 4002 and the ulna 4004.

Fractures of the Rib

Figure 42:
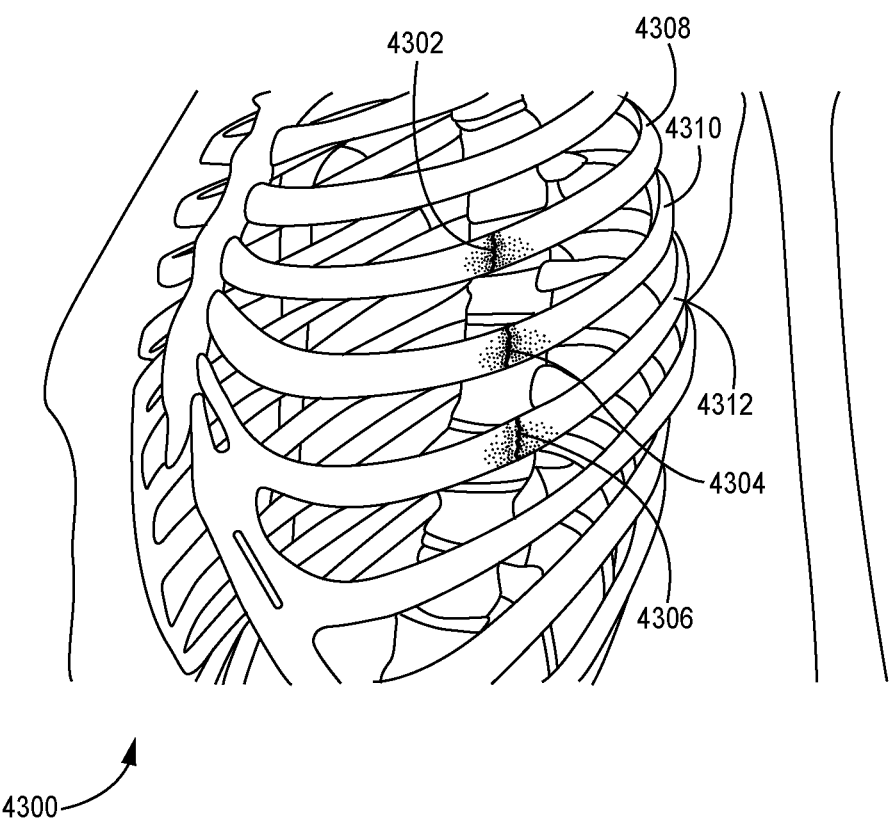
FIG. 42 is a view of a human rib cage with rib fractures that can be fixated with one or more rodscrews of FIG. 1, 5, or 6, according to an embodiment.

FIG. 42 is a view of a human rib cage 4300 with fractures 4302, 4304, and 4306 in three ribs 4308, 4310, and 4312, respectively, where each of the fractures can be fixated with one or more rodscrews 100, 600, or 700 of FIG. 1 or 5-6, according to an embodiment. For purposes of example, the described procedures for treating a rib fracture are described as using one or more rodscrews 100 of FIG. 1, it being understood that the procedures may be similar if one or more rodscrews 600 and 700 are used with, or instead of, the one or more rodscrews 100.

The conventional treatment for most rib fractures is to let the fracture heal on its own over the normal healing time of six to eight weeks.

But a potential, and serious, complication of a rib fracture is pneumonia caused by a subject breathing shallowly to avoid the pain that the rib fracture causes as the chest expands and contracts. For example, this pain is due to the sections of the rib 4308 on either side of the fracture 4302 moving relative to one another as the diaphragm contracts and the lungs expand the rib cage as they fill with air, and as the rib cage contracts as the diaphragm relaxes to expel air from the lungs.

For more serious rib fractures, a surgeon (not shown in FIG. 42) may implant a plate across the fracture to stabilize the positions of the sections of the rib on either side of the fracture.

Although the plate may reduce the pain caused by the fracture during breathing, implanting the plate typically requires a relatively large incision during implantation and during removal of the plate (if the plate is removed).

Referring to FIGS. 1 and 42, in an embodiment, a surgeon (not shown in FIGS. 1 and 42) implants one or more rodscrews 100 inside of the rib of an adult subject to stabilize the positions of the sections of the rib on either side of the fracture, and, therefore, to promote healing of the fracture with reduced pain. Therefore, implanting a rodscrew 100 has the healing-promoting and pain-decreasing benefits of a plate without the need for large incisions for implant and removal, respectively.

For purposes of example, a procedure for fixating the fracture 4302 in the rib 4308 is described, it being understood that respective procedures for fixating the fractures 4304 and 4306 in the ribs 4310 and 4312 can be similar.

Still referring to FIGS. 1 and 42, in an embodiment, a surgeon (not shown in FIGS. 1 and 42) implants a rodscrew 100 into the fractured rib 4308, in a manner similar to the manner described above for spinal fusion in conjunction with FIGS. 9-12, such that the rodscrew spans one or more fractures, including the fracture 4302, in the rib. Because the rodscrew 100 is flexible while unlocked, the rodscrew can traverse and occupy a curved path within the rib 4308.

Next, the surgeon (not shown in FIGS. 1 and 42) screws or hammers the rodscrew 100 so that the distal end 102 engages a respective portion of the rib 4308 on the distal side (the side opposite the side of entry of the rodscrew into the rib) of the fracture 4302, and so that the proximal end 106 of the rodscrew 100 engages the opening (not shown in FIGS. 1 and 42) in the rib through which the surgeon implanted the rodscrew, the opening being on the proximal side of the fracture.

Then, the surgeon (not shown in FIGS. 1 and 42) transitions the rodscrew 100 from a flexible state to a rigid state to lock the rodscrew in its curved shape so that the rodscrew holds the spanned sections of the rib 4308 together to promote healing of the one or more fractures including the fracture 4302.

Because the rodscrew 100 stabilizes the positions of the sections of the fractured rib 4308, the rodscrew may reduce the subject's pain by reducing the movement of the rib sections relative to one another during expansion and contraction of the subject's chest.

Furthermore, a surgeon (not shown in FIGS. 1 and 42) need only make a relatively small incision and hole in the rib bone 4308 to implant the rodscrew 100, and need only make another relatively small incision to remove the rodscrew after the fracture 4302 has healed (if the rodscrew is to be removed).

In an alternate embodiment, because a rib bone, such as the ribs 4308, 4310, and 4312, is relatively narrow, a surgeon may ream a path within the intramedullary space of the rib using a guidewire (not shown in FIGS. 1 and 42), but may insert a rodscrew 100 into the reamed path without using a guidewire, in a manner similar to that described above for treating mandible fractures in conjunction with FIGS. 28-30.

And, as described above for treating mandible fractures in conjunction with FIGS. 28-30, inserting a rodscrew 100 into a reamed path without using a guidewire allows use of a rodscrew that has no receptacle for a guidewire, and the lack of a guidewire receptacle allows the rodscrew to be narrower (e.g., to have a smaller diameter) than it would be if it were to include a guidewire opening or bore.

Referring to FIG. 42, alternate embodiments of a technique for treating fractures of, and procedures related to, a rib (e.g., the rib 4308) are contemplated. For example, embodiments described in conjunction with FIGS. 1-41 may be applicable to a technique for treating fractures of, and procedures related to, a rib.

Referring to FIGS. 1-42, in summary, potential advantages of rodscrew usage for one or more of the aforementioned procedures versus existing techniques and devices include:

Smaller skin incisions required for implantation
Reduced surgical time
Reduced blood loss due to surgery
Quicker patient recovery
Stronger holding forces and reduced need for revision surgery
Ability to unlock and remove the rodscrew at a later date

EXAMPLE EMBODIMENTS

Example 1 includes a bone-fracture fixation device, comprising: a flexible body; a plurality of flexible members disposed longitudinally within the flexible body, such that the flexible body is rigid when the flexible members are fixed into position; and first and second interfaces respectively coupled to the flexible body, each of at least one of the first and second interfaces including a respective at least one hole each configured to receive a respective attachment member configured to engage a bone.

Example 2 includes the device of Example 1 wherein each of at least one the first and second interfaces includes a respective at least one tab each configured to engage a respective one of at least one pocket of the flexible body.

Example 3 includes the device of any of Examples 1-2 wherein each of at least one of the first and second interfaces includes a respective at least one pocket each configured to engage a respective one of at least one tab of the flexible body.

Example 4 includes the device of any of Examples 1-3 wherein each of at least one of the first and second interfaces further comprises a respective intermediate portion disposed between a respective first interface end and a respective second interface end and tapered inward from the respective first interface end to the respective second interface end.

Example 5 includes the device of any of Examples 1-4 wherein: each of at least one of the first and second interfaces further includes a respective longitudinal axis that extends between respective first and second interface ends; and at least one of the at least one hole of each of at least one of the first and second interfaces intersects the respective longitudinal axis.

Example 6 includes the device of any of Examples 1-5 wherein: each of at least one of the first and second interfaces further includes a respective longitudinal axis that extends between respective first and second interface ends; and at least one of the at least one hole of each of at least one of the first and second interfaces is approximately perpendicular to the respective longitudinal axis.

Example 7 includes the device of any of Examples 1-6 wherein: each of at least one of the first and second interfaces further includes a respective longitudinal axis that extends between respective first and second interface ends; and at least one of the at least one hole of each of at least one of the first and second interfaces intersects the respective longitudinal axis at an acute angle.

Example 8 includes the device of any of Examples 1-7 wherein: each of at least one of the first and second interfaces further includes a respective longitudinal axis that extends between respective first and second interface ends; and at least one of the at least one hole of each of at least one of the first and second interfaces intersects the respective longitudinal axis at an obtuse angle.

Example 9 includes the device of any of Examples 1-8 wherein each of at least one of the at least one hole is threaded and is configured to receive a respective locking screw as the attachment member.

Example 10 includes the device of any of Examples 1-9 wherein each of at least one of the at least one hole is configured to receive a respective locking screw as the attachment member.

Example 11 includes the device of any of Examples 1-10 wherein each of at least one of the at least one hole has a smooth wall and is configured to receive a respective locking screw as the attachment member.

Example 12 includes the device of any of Examples 1-11 wherein: each of at least one of the first and second interfaces further includes a respective longitudinal axis that extends between respective first and second interface ends; and first and second ones of the at least one hole of each of at least one of the first and second interfaces are approximately perpendicular to a respective longitudinal axis and to one another.

Example 13 includes the device of any of Examples 1-12 wherein: each of at least one of the first and second interfaces further includes a respective longitudinal axis that extends between respective first and second interface ends; and first and second ones of the at least one hole of each of at least one of the first and second interfaces are approximately perpendicular to a respective longitudinal axis and are at an angle of approximately 45° relative to one another.

Example 14 includes the device of any of Examples 1-13 wherein: each of at least one of the first and second interfaces further includes a respective longitudinal axis that extends between respective first and second interface ends; and first and second ones of the at least one hole of each of at least one of the first and second interfaces are approximately perpendicular to a respective longitudinal axis and are at an angle of approximately 60° relative to one another.

Example 15 includes the device of any of Examples 1-14 wherein: each of at least one of the first and second interfaces further includes a longitudinal axis that extends between respective first and second interface ends; and first and second ones of the at least one hole of each of at least one of the first and second interfaces are approximately perpendicular to a respective longitudinal axis and are at an angle of approximately 90° relative to one another.

Example 16 includes the device of any of Examples 1-15 wherein: each of at least one of the first and second interfaces further includes a respective longitudinal axis that extends between respective first and second interface ends; and first and second ones of the at least one hole of each of at least one of the first and second interfaces are approximately perpendicular to a respective longitudinal axis and are approximately parallel to one another.

Example 17 includes a bone-fracture fixation device, comprising: a first interface configured to engage a bone and including at least one hole each configured to receive a respective attachment member; a second interface configured to engage a bone; a body including a series of beads disposed between, and coupled to, the first interface and the second interface, each bead in the series of beads including three or more fiber bores; three or more fibers each disposed in a respective one of the fiber bores; and a locking interface disposed adjacent to one of the first and second interfaces, configurable to hold the fibers to cause the body to be rigid in a curved configuration, and configurable to release the fibers to cause the body to be flexible.

Example 18 includes the device of Example 17 wherein: the first interface includes a distal interface; the second interface includes a proximal interface; and the locking interface is disposed adjacent to the proximal interface.

Example 19 includes the device of any of Examples 17-18 wherein: the first interface includes a proximal interface; the second interface includes a distal interface; and the locking interface is disposed adjacent to the proximal interface.

Example 20 includes the device of any of Examples 17-19 wherein each of at least one of the at least one hole is threaded and is configured to receive a locking screw.

Example 21 includes the device of any of Examples 17-20 wherein each of at least one of the at least one hole is configured to receive a locking screw.

Example 22 includes the device of any of Examples 17-21 wherein each of at least one of the least one hole has a smooth wall and is configured to receive a locking screw.

Example 23 includes the device of any of Examples 17-22 wherein the first interface comprises a distal interface that is tapered from a widest portion adjacent to the body to a narrowest portion remote from the body.

Example 24 includes the device of any of Examples 17-23 wherein: the body has a body width; and the first interface comprises a distal interface having a widest portion adjacent to the body and being at least as wide as the body width, having a narrowest portion remote from the body, and being tapered from the widest portion to the narrowest portion.

Example 25 includes the device of any of Examples 17-24 wherein: the first interface comprises a proximal interface having a housing; the second interface comprises a distal interface; and the locking interface is disposed inside of the housing of the proximal interface.

Example 26 includes the device of any of Examples 17-25 wherein: the first interface comprises a distal interface; the second interface comprises a proximal interface having a housing; and the locking interface is disposed inside of the housing of the proximal interface.

Example 27 includes a method, comprising: forming a curved pathway in a respective intramedullary space of each of at least one bone; inserting, into the curved pathway, a bone-fracture fixation device in a flexible configuration; inserting each of at least one attachment member through a respective hole in at least one interface at at least one end of the bone-fracture fixation device and into a bone; and transitioning the bone-fracture fixation device from the flexible configuration to a rigid configuration while the bone-fracture fixation device has a curved shape.

Example 28 includes the method of Example 27 wherein forming the curved pathway comprises: forming a hole in one of the at least one bone; inserting a guide wire through the hole and through the respective intramedullary space of each of at least one bone; and reaming the curved pathway by moving a reamer over the guide wire.

Example 29 includes the method of any of Examples 27-28 wherein inserting the bone-fracture fixation device includes: inserting, into the curved pathway, a guidewire; and inserting the bone-fracture fixation device over the guidewire.

Example 30 includes the method of any of Examples 27-29 wherein inserting each of at least one attachment member includes inserting each of at least one screw through the respective hole and driving each of the at least one screw into a bone.

Example 31 includes the method of any of Examples 27-30 wherein inserting each of at least one attachment member includes driving each of at least one screw through the respective hole and into a bone.

From the foregoing it will be appreciated that, although specific embodiments have been described herein for purposes of illustration, various modifications may be made without deviating from the spirit and scope of the disclosure. Furthermore, where an alternative is disclosed for a particular embodiment, this alternative may also apply to other embodiments even if not specifically stated. Moreover, one or more components of a described apparatus or system, or one or more steps of a described method, may have been omitted from the description for clarity or for another reason. In addition, one or more components of a described apparatus or system that have been included in the description may be omitted from the apparatus or system, and one or more steps of a described method that have been included in the description may be omitted from the method.

The invention claimed is:

1. A method, comprising:
   forming a curved pathway in an intramedullary space of a pelvic bone;
   inserting, into the curved pathway, a bone-fracture fixation device in a flexible configuration, the bone-fracture fixation device having a proximal end portion and a distal end portion;
   securing the distal end portion of the bone-fracture fixation device along the curved pathway within the intramedullary space;
   securing the proximal end portion of the bone-fracture fixation device to an artificial hip socket positioned at a native acetabulum of the pelvic bone; and
   transitioning the bone-fracture fixation device from the flexible configuration to a rigid configuration while the bone-fracture fixation device has a curved shape.

2. The method of claim 1, wherein forming the curved pathway comprises:
   forming a hole in the pelvic bone;
   inserting a guide wire through the hole and through the intramedullary space of the pelvic bone; and reaming the curved pathway by moving a reamer over the guide wire.

3. The method of claim 1, wherein inserting the bone-fracture fixation device includes:
inserting, into the curved pathway, a guidewire; and
inserting the bone-fracture fixation device over the guidewire.

4. The method of claim 1, wherein securing the distal end portion of the bone-fracture fixation device along the curved pathway comprises securing the distal end portion of the bone-fracture fixation device in the ilium of the pelvic bone.

5. The method of claim 1, wherein securing the distal end portion of the bone-fracture fixation device along the curved pathway comprises securing the distal end portion of the bone-fracture fixation device in the ischium of the pelvic bone.

6. The method of claim 1, wherein securing the distal end portion of the bone-fracture fixation device along the curved pathway comprises securing the distal end portion of the bone-fracture fixation device in the pubis of the pelvic bone.

7. A method, comprising:
forming a first curved pathway in an intramedullary space of a pelvic bone;
positioning, along the first curved pathway, a first fixation device in a flexible configuration, the first fixation device having a first proximal end portion and a first distal end portion,
securing the first proximal end portion of the first fixation device to an artificial hip socket positioned at a native acetabulum of the pelvic bone;
forming a second curved pathway in the intramedullary space of the pelvic bone;
positioning, along the second curved pathway, a second fixation device in a flexible configuration, the second fixation device having a second proximal end portion and a second distal end portion;
securing the second proximal end portion of the second fixation device to the artificial hip socket positioned at the native acetabulum;
transitioning the first fixation device from the flexible configuration to a rigid configuration while the first fixation device has a curved shape; and
transitioning the second fixation device from the flexible configuration to a rigid configuration while the second fixation device has a curved shape.

8. The method of claim 7, further comprising securing the first distal end portion in the ilium of the pelvic bone.

9. The method of claim 7, further comprising securing the first distal end portion in the ischium of the pelvic bone.

10. The method of claim 7, further comprising securing the first distal end portion in the pubis of the pelvic bone.

11. The method of claim 7, further comprising:
securing the first distal end portion of the first fixation device in the ilium of the pelvic bone, and
securing the second distal end portion of the second fixation device in the ischium of the pelvic bone.

12. The method of claim 7, further comprising:
securing the first distal end portion of the first fixation device in the ilium of the pelvic bone, and
securing the second distal end portion of the second fixation device in the pubis of the pelvic bone.

13. The method of claim 7, further comprising:
securing the first distal end portion of the first fixation device in the ischium of the pelvic bone, and
securing the second distal end portion of the second fixation device in the pubis of the pelvic bone.

14. The method of claim 13, wherein the first, second, and third fixation devices are evenly spaced around a periphery of the artificial hip socket.

15. The method of claim 7, further comprising:
forming a third curved pathway in the intramedullary space of the pelvic bone,
positioning, along the third curved pathway, a third fixation device in a flexible configuration, the third fixation device having a third proximal end portion and a third distal end portion,
securing the third proximal end portion of the third fixation device to the artificial hip socket positioned at the native acetabulum, and
transitioning the third fixation device from the flexible configuration to a rigid configuration while the third fixation device has a curved shape.

16. The method of claim 15, further comprising:
securing the first distal end portion of the first fixation device in the ilium of the pelvic bone,
securing the second distal end portion of the second fixation device in the ischium of the pelvic bone, and
securing the third distal end portion of the third fixation device in the pubis of the pelvic bone.

17. The method of claim 15, wherein the first, second, and third fixation devices form a tripod like structure to secure the artificial hip socket in place against the acetabulum.

18. A method, comprising:
positioning a first fixation device, in a flexible configuration, along a first curved pathway within an intramedullary space of a pelvic bone, wherein a portion of the first fixation device is positioned at a periphery of an acetabulum of the pelvic bone and another portion of the first fixation device is positioned in one of an ilium, an ischium, or a pubis of the pelvic bone;
positioning a second fixation device, in a flexible configuration, along a second curved pathway within the intramedullary space of the pelvic bone, wherein a portion of the second fixation device is positioned at or near the acetabulum and another portion of the second fixation device is positioned in a different one of the ilium, the ischium, or the pubis of the pelvic bone than the one of the ilium, the ischium, and the pubis in which the first fixation device is secured;
transitioning the first fixation device from the flexible configuration to a rigid configuration while the first fixation device has a curved shape; and
transitioning the second fixation device from the flexible configuration to a rigid configuration while the second fixation device has a curved shape.

19. The method of claim 18, further comprising:
positioning a third fixation device, in a flexible configuration, along a third curved pathway within the intramedullary space of the pelvic bone, wherein a portion of the third fixation device is positioned at the periphery the acetabulum and another portion of the third fixation device is positioned in a different one of the ilium, the ischium, or the pubis of the pelvic bone than the ones of the ilium, the ischium, and the pubis in which the first and second fixation devices are respectively secured;
transitioning the third fixation device from the flexible configuration to a rigid configuration while the third fixation device has a curved shape.

20. The method of claim 19, wherein the first, second, and third fixation devices form a tripod like structure to secure an artificial hip socket in place adjacent the acetabulum.

21. The method of claim 19, wherein the first, second, and third fixation devices are evenly spaced around a periphery of the acetabulum.

\* \* \* \* \*